(12) United States Patent
Oskin et al.

(10) Patent No.: US 9,211,141 B2
(45) Date of Patent: Dec. 15, 2015

(54) VAGINAL MANIPULATOR

(71) Applicant: BOSTON SCIENTIFIC SCIMED, INC., Maple Grove, MN (US)

(72) Inventors: Christopher L. Oskin, Grafton, MA (US); Michael F. Weiser, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/828,215

(22) Filed: Mar. 14, 2013

(65) Prior Publication Data

US 2013/0274759 A1    Oct. 17, 2013

Related U.S. Application Data

(60) Provisional application No. 61/623,772, filed on Apr. 13, 2012.

(51) Int. Cl.
*A61B 17/42* (2006.01)
*A61F 2/00* (2006.01)
(Continued)

(52) U.S. Cl.
CPC ............. *A61B 17/42* (2013.01); *A61B 17/0469* (2013.01); *A61B 17/062* (2013.01);
(Continued)

(58) Field of Classification Search
CPC .. A61B 17/42; A61B 17/0469; A61B 17/062; A61B 2017/00805; A61B 2017/047; A61B 2017/0472; A61B 17/0491; A61B 17/06066; A61B 2017/06042; A61B 2017/06095; A61B 17/3417; A61B 17/3496; A61F 2/0063; A61F 2002/0072; A61F 2002/0045

USPC ........ 606/119, 139, 141, 144, 148, 151, 185, 606/186, 187, 193, 222
See application file for complete search history.

(56) References Cited

U.S. PATENT DOCUMENTS 4,172,458 A * 10/1979 Pereyra ................. 606/144
5,320,632 A *  6/1994 Heidmueller ............ 606/144
(Continued)

FOREIGN PATENT DOCUMENTS

WO    2009073619 A2    6/2009
WO    2013155304 A1    10/2013

OTHER PUBLICATIONS

Search Report and Written Opinion for International Application No. PCT/US2013/036170, mailed Sep. 3, 2013, 12 pages.
(Continued)

*Primary Examiner* — Katherine Rodjom
*Assistant Examiner* — Christian Knauss
(74) *Attorney, Agent, or Firm* — Brake Hughes Bellermann LLP

(57) ABSTRACT

The present invention discloses a vaginal manipulator configured to be inserted through a vaginal opening. The vaginal manipulator includes an elongated portion having a proximal end portion and a distal end portion. The elongated portion has an actuating mechanism. The vaginal manipulator further includes a head portion extending from the distal end portion of the elongated portion. The head portion includes a linear piercing member. The piercing member is configured to temporarily help retain a bodily implant proximate an outer surface of a vaginal wall. The piercing member is configured to move from a retracted position to an extended position with respect to the head portion. Further, the actuating mechanism is operatively coupled to the piercing member and is configured to move the piercing member from its retracted position to its extended position.

18 Claims, 14 Drawing Sheets

(51) Int. Cl.
   *A61B 17/062* (2006.01)
   *A61B 17/04* (2006.01)
   *A61B 17/06* (2006.01)
   *A61B 17/00* (2006.01)

(52) U.S. Cl.
   CPC ............ *A61F 2/0045* (2013.01); *A61F 2/0063* (2013.01); *A61B 17/0491* (2013.01); *A61B 17/06066* (2013.01); *A61B 2017/00805* (2013.01); *A61B 2017/047* (2013.01); *A61B 2017/0472* (2013.01); *A61B 2017/06042* (2013.01); *A61B 2017/06095* (2013.01); *A61F 2002/0072* (2013.01)

(56) References Cited

U.S. PATENT DOCUMENTS

| | | | | |
|---|---|---|---|---|
| 5,370,675 | A * | 12/1994 | Edwards et al. | 607/101 |
| 5,374,275 | A * | 12/1994 | Bradley et al. | 606/144 |
| 5,403,329 | A * | 4/1995 | Hinchcliffe | 606/147 |
| 5,439,467 | A | 8/1995 | Benderev et al. | |
| 5,474,543 | A * | 12/1995 | McKay | 604/272 |
| 5,507,754 | A * | 4/1996 | Green et al. | 606/139 |
| 5,507,755 | A * | 4/1996 | Gresl et al. | 606/139 |
| 5,507,757 | A * | 4/1996 | Sauer et al. | 606/144 |
| 5,588,960 | A * | 12/1996 | Edwards et al. | 604/20 |
| 5,662,664 | A * | 9/1997 | Gordon et al. | 606/144 |
| 6,056,744 | A * | 5/2000 | Edwards | 606/41 |
| 6,096,051 | A * | 8/2000 | Kortenbach et al. | 606/144 |
| 6,156,006 | A * | 12/2000 | Brosens et al. | 604/104 |
| 6,254,598 | B1 * | 7/2001 | Edwards et al. | 606/41 |
| 6,293,952 | B1 * | 9/2001 | Brosens et al. | 606/119 |
| 6,312,437 | B1 * | 11/2001 | Kortenbach | 606/139 |
| 6,695,855 | B1 * | 2/2004 | Gaston | 606/151 |
| 6,741,895 | B1 * | 5/2004 | Gafni et al. | 607/138 |
| 7,615,049 | B2 * | 11/2009 | West et al. | 606/41 |
| 7,918,795 | B2 * | 4/2011 | Grossman | 600/439 |
| 8,460,171 | B2 * | 6/2013 | von Pechmann et al. | 600/37 |
| 2002/0050277 | A1 * | 5/2002 | Beyar | 128/898 |
| 2004/0068273 | A1 * | 4/2004 | Fariss et al. | 606/144 |
| 2004/0111102 | A1 * | 6/2004 | Saller et al. | 606/151 |
| 2004/0193238 | A1 * | 9/2004 | Mosher et al. | 607/99 |
| 2005/0283189 | A1 * | 12/2005 | Rosenblatt | 606/216 |
| 2006/0265042 | A1 | 11/2006 | Catanese et al. | |
| 2006/0265842 | A1 | 11/2006 | Hoffman et al. | |
| 2007/0005018 | A1 * | 1/2007 | Tekbuchava | 604/164.01 |
| 2009/0023982 | A1 * | 1/2009 | Karram | 600/37 |
| 2009/0171143 | A1 * | 7/2009 | Chu et al. | 600/37 |
| 2009/0312772 | A1 | 12/2009 | Chu | |
| 2010/0114087 | A1 * | 5/2010 | Edwards et al. | 606/33 |
| 2010/0280530 | A1 * | 11/2010 | Hashiba | 606/144 |
| 2011/0190792 | A1 | 8/2011 | Chu | |

OTHER PUBLICATIONS

International Preliminary Report on Patentability for International Application No. PCT/US2013/036170, mailed Oct. 23, 2014, 9 pages.

* cited by examiner

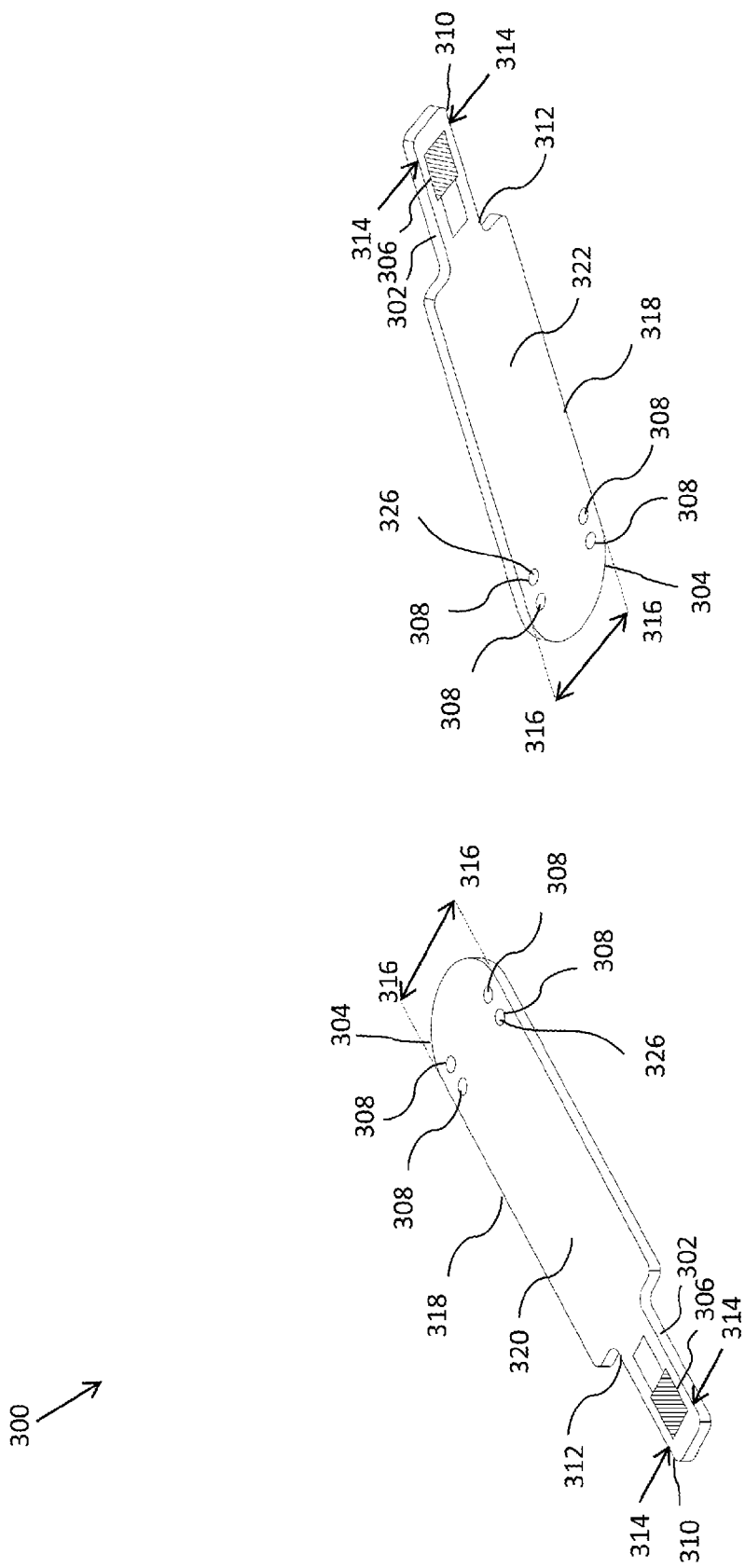

VAGINAL MANIPULATOR

CROSS-REFERENCE TO RELATED APPLICATION

This application is a Nonprovisional of, and claims priority to, U.S. Patent Application No. 61/623,772, filed on Apr. 13, 2012, entitled "VAGINAL MANIPULATOR", which is incorporated by reference herein in its entirety.

BACKGROUND

1. Field

The present invention generally relates to medical devices and procedures, particularly devices and methods used during surgery for the treatment of pelvic floor disorders.

2. Description of the Related Art

A pelvic floor disorder may occur when pelvic muscles and connective tissues in the pelvis weaken or are injured. Disorders may result from pelvic surgery, radiation treatments, and, in some cases, pregnancy or vaginal delivery of a child. There are a variety of problems related to the pelvic floor. Some of the common problems include pelvic organ prolapse such as vaginal prolapse, urinary incontinence, and anal incontinence.

Various types of tissue manipulators are used for manipulating pelvic and other organs to facilitate access to their anatomical structures during surgical procedures. A vaginal manipulator is one such manipulator that can be introduced into a vagina for manipulating vaginal tissues. The purpose of some vaginal manipulators is to assist in suturing of an implant to a body tissue as outer surfaces of the manipulators may act as a backstop for suturing during abdominal or laparoscopic pelvic floor procedures. However, during suturing, a mere use of the surfaces of the manipulators may not properly allow holding the implant at the surface and facilitate suturing. Therefore, suturing and holding the implant at a target tissue site may be time consuming and difficult.

Thus, there is a need for an improved medical device or a manipulator having a facility or provision to facilitate fixation and suturing of implants to bodily tissues.

SUMMARY

In an embodiment, the present invention discloses a vaginal manipulator configured to be inserted through a vaginal opening. The vaginal manipulator includes an elongated portion having a proximal end portion and a distal end portion. The elongated portion has an actuating mechanism. The vaginal manipulator further includes a head portion extending from the distal end portion of the elongated portion. The head portion includes a linear piercing member. The piercing member is configured to temporarily help retain a bodily implant proximate an outer surface of a vaginal wall. The piercing member is configured to move from a retracted position to an extended position with respect to the head portion. Further, the actuating mechanism is operatively coupled to the piercing member and is configured to move the piercing member from its retracted position to its extended position.

In another embodiment, the present invention discloses a vaginal manipulator configured to be inserted through a vaginal opening. The vaginal manipulator includes an elongated portion having a proximal end portion and a distal end portion. The elongated portion has an actuating mechanism. The vaginal manipulator further includes a head portion extending from the distal end portion of the elongated portion. The head portion is configured to contact an inner surface of a vaginal wall. The head portion includes a piercing member configured to move between a retracted position and an extended position with respect to the head portion. The vaginal manipulator further includes a suture coupled to the piercing member such that the piercing member is configured to move the suture through the vaginal wall when the piercing member is moved from the retracted position to the extended position, thereby affixing a bodily implant coupled to the suture to the outer surface of the vaginal wall.

In yet another embodiment, the present invention discloses a method for fixing a bodily implant to an outer surface of a vaginal wall. The method includes advancing a vaginal manipulator into a vaginal opening. The vaginal manipulator has a piercing member provided on the head portion of the vaginal manipulator. The vaginal manipulator is configured to move from within the head portion to a location external to the head portion. The method further includes placing a bodily implant through an abdominal incision laparoscopically over a portion of an outer surface of the vaginal wall. The method further includes moving the piercing member from a retracted position to an extended position with respect to the head portion of the vaginal manipulator such that the piercing member protrudes outward with respect to the head portion and pierces through the vaginal wall, when in the extended position. The method further includes suturing the bodily implant on the outer surface of the vaginal wall. Upon suturing the bodily implant on the outer surface of the vaginal wall, the piercing member is moved from the extended position to the retracted position with respect to the head portion such that the piercing member comes out of the vaginal wall.

BRIEF DESCRIPTION OF THE FIGURES

The invention and the following detailed description of certain embodiments thereof may be understood with reference to the following figures:

FIGS. 3A and 3B are perspective views of a vaginal manipulator in different orientations, in accordance with an embodiment of the present invention.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

In general, the invention is directed to systems, methods, and devices for treating pelvic floor disorders such as pelvic organ prolapse, urinary incontinence, anal incontinence, and the like. As described below, in some illustrative embodiments, the invention provides systems, methods, and devices employing an improved manipulator configured to help maneuver a vagina of a patient facilitating proper dissection in the pelvis and also facilitating in suturing of a bodily implant.

The term patient may hereafter be used for a person who benefits from the medical device or the methods disclosed in the present invention. For example, the patient can be a person whose body is operated through the medical device or the method disclosed by the present invention. The patient can be a male, a female or any other mammal.

The terms proximal and distal described in relation to various devices, apparatuses, and components (as discussed in the subsequent text of the present invention) are referred with a point of reference. The point of reference, as used in this description, is a perspective of an operator. The operator may be a surgeon, a physician, a nurse, a doctor, a technician, and the like, who may perform the procedure and operate the medical device as described in the present invention. The term proximal refers to an area or portion that is closer or closest to the operator during a surgical procedure. The term distal refers to an area or portion that is farther or farthest from the operator.

Figure 1:
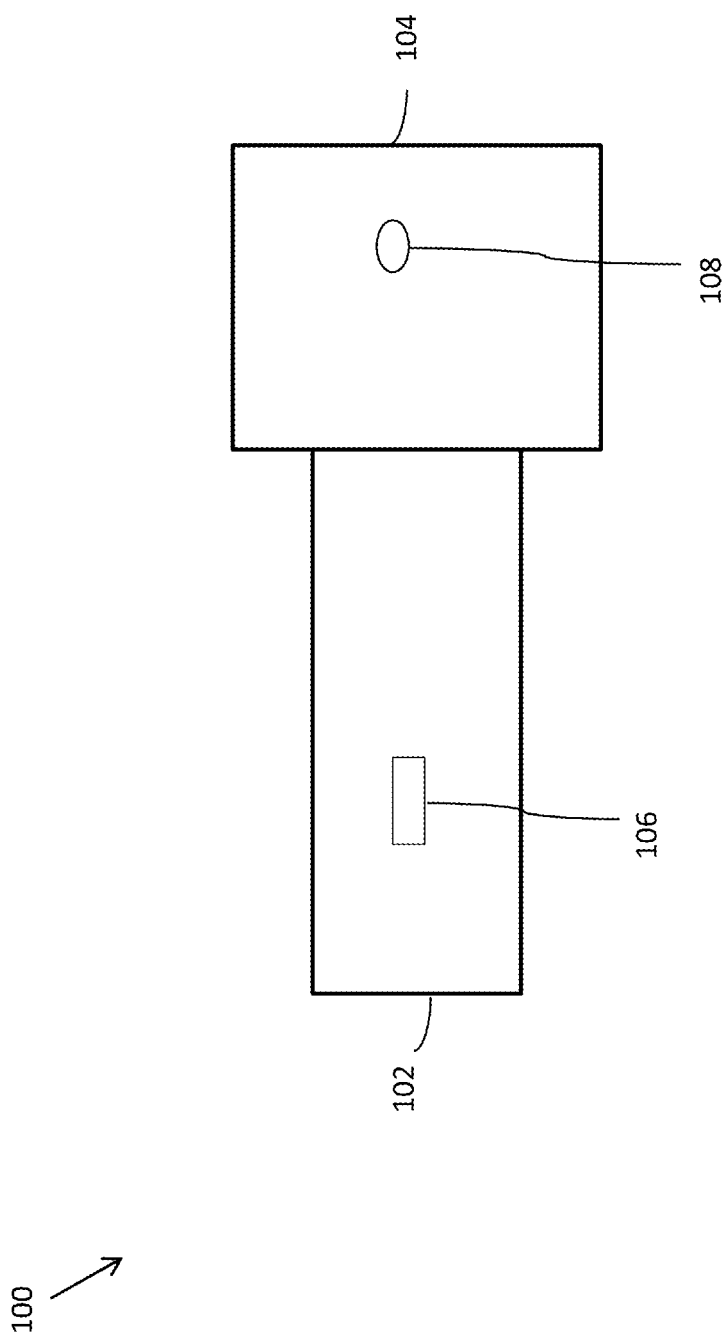
FIG. 1 is a schematic diagram of a vaginal manipulator, in accordance with an embodiment of the present invention.

FIG. 1 is a schematic diagram of a vaginal manipulator 100 configured to be inserted through a vaginal opening and facilitate placement of a bodily implant to a bodily tissue. The vaginal manipulator 100 includes an elongated portion 102 and a head portion 104 extending from the elongated portion 102.

The elongated portion 102 includes a proximal end portion and a distal end portion. In some embodiments, the elongated portion 102 may have a predefined width referred to as first width. In some embodiments, the elongated portion 102 can be a handle of the vaginal manipulator 100 configured to be held by an operator external from a body tissue. In certain embodiments, the elongated portion 102 may be cylindrical in shape having a circular cross section at the distal end portion and the proximal end potion. In other embodiments, the elongated portion 102 may be shaped such that the cross section is rectangular, or square, or any other shape at its distal end portion and the proximal end portion. Similarly, various other shapes of the elongated portion 102 are possible. For example, the cross section of the proximal and the distal end portions can be rectangular, pentagonal, hexagonal, octal, and the like. In accordance with some embodiments, the width of the elongated portion 102 is uniform from the proximal end portion to the distal end portion. In accordance with other embodiments, the elongated portion 102 may be tapered. In some embodiments, the elongated portion 102 is flexible in nature. In other embodiments, the elongated portion 102 is rigid.

The elongated portion 102 further includes an actuating mechanism 106 as discussed later. The actuating mechanism 106 can include one of a lever, a knob, a slider, a rotator and the like provided on the elongated portion 102 that are discussed below.

The head portion 104 may extend from the distal end portion of the elongated portion 102. In some embodiments, the head portion 104 may have a second width such that the second width is greater than the first width (of the elongated portion 102). In this manner, the head portion 104 projects/bulges laterally from the elongated portion 102 and provides even a larger surface area for tissue manipulation and suturing through the head portion 104. In some other embodiments, the first width of the elongated member 102 and the second width of the head portion 104 may be same or substantially same. In some embodiments, the head portion 104 may be tubular in shape. In some other embodiments, the head portion 104 may be circular, cylindrical, flat, or any of other shape.

In some embodiments, the head portion 104 may include a first surface on an outer side of the head portion 104 and a second surface on an inner side opposite the first surface. In some embodiments, the surgeon/operator may use the first surface to suture on anterior portions of the vagina and the second surface to suture on posterior portions of the vagina. In some embodiments, one or both of the first surface and the second surface may be tubular in shape. In some other embodiments, one or both of the first surface and the second surface may be circular, cylindrical, flat, or of any other shape.

The head portion 104 includes a piercing member 108. In some embodiments, the head portion 104 includes a linear piercing member. In other embodiments, the head portion 104 includes a piercing member 108 with any other shape or profile such as a curved shape or profile. The piercing member 108 is configured to temporarily help retain a bodily implant proximate an outer surface of a vaginal wall. The piercing member 108 is further configured to move from a retracted position to an extended position with respect to the head portion 104.

In some embodiments, the piercing member 108 is disposed and fitted within the head portion 104 of the vaginal manipulator 100 such that the piercing member 108 may move from a location internal to the head portion 104 to a location external to the head portion 104 of the vaginal manipulator 100. The head portion 104 may include at least one hole that defines a lumen such that the piercing member 108 may be extended from the at least one hole.

In some embodiments, the piercing member 108 is disposed and fitted within the head portion 104 in such a manner such that the piercing member 108 is configured to extend from a location internal to the head portion 104 toward the first surface and past the first surface to extend beyond the first surface. In some embodiments, the piercing member 108 is disposed and fitted within the head portion 104 in such a manner that the piercing member 108 is configured to extend from a location internal to the head portion 104 toward the second surface and past the second surface to extend beyond the second surface.

In some embodiments, the piercing member 108 may be or further include a needle such that the needle is configured to extend from internal to the head portion 104 and toward respective surfaces such as the first surface and the second surface and past the first and the second surface. The needle that extends toward the first surface can be termed as a first needle and the needle that extends toward the second surface can be termed as a second needle. The first surface and the second surface are disposed or face substantially opposite to one another and so tip portions of the first needle and the second needle may face opposite one another. The first surface and the second surface can, in some embodiments, be the top and bottom surfaces of the head portion 104, respectively. In other embodiments, the first needle and the second needle face or extend in different directions, but no opposite directions. For example, the needles may extend at angles with respect to the first and second surfaces. In other embodiments, the first and second surfaces are not disposed opposite one another. For example, one surface may be disposed at an angle with respect to another surface.

In some embodiments, the piercing member 108 may include more than one needle. For example, the piercing member 108 configured to extend toward the first surface from within the head portion 104 may include more than one needle similar to the first needle. Similarly, the piercing member 108 configured to extend toward the second surface from within the head portion 104 may include more than one needle similar to the second needle. In certain embodiments, the piercing member 108 can be a surgical needle configured to pierce through the patient's body during insertion. The surgical needle may be made of a metal such as stainless steel and the like. In other embodiments, the piercing member 108 can be a nail, a pin, and the like. In some embodiments, the piercing member 108 may be shaped as a curved or straight pointed portion. The piercing member 108 can have a variety of shapes and sizes depending on the surgical requirements.

The actuating mechanism 106 provided on the elongated portion 102 is configured to move the piercing member 108 from its retracted position to its extended position. In the retracted position, the piercing member 108 may not be exposed to bodily tissues such that the piercing member 108 may be submerged with respect to the head portion 104. In the retracted position, a substantial length of the piercing member 108 goes inside the head portion 104. For example, in some embodiments, a tip portion of the piercing member 108 enters into the head portion 104. In the extended position, the piercing member 108 is configured to protrude with respect to the head portion 104. In the extended position, a substantial length of the piercing member 108 comes out of the head portion 104. For example, the tip portion of the piercing member 108 may come out of the head portion 104 to a defined extent or length that depends on an amount of adjustment made by the actuating mechanism 106.

Various types of actuating mechanisms 106 may be deployed that can be configured to move the piercing member 108 between the retracted position and the extended position. For example, in some embodiments, the piercing member 108 can be slidably actuated to move between the extended and the refracted positions. In such cases, springs and various other linkages that are configured to cause a slidable movement may be used in the actuating mechanism 106. Similarly, various other types of actuating mechanisms 106 may also be used. The actuating mechanism 106 can also include one of a lever, a knob, a slider, a rotator and the like for causing an actuation of the piercing member 108.

In some embodiments, the actuating mechanism 106 is operatively coupled to the piercing member 108. For example, the head portion 104 and the elongated portion 102 may include a lumen such that the actuating mechanism 106 or a portion of the actuating mechanism 106 is disposed within the lumen. The actuating mechanism 106 extends through at least a portion of length of the lumen and gets operatively coupled to the piercing member 108 disposed within the head portion 104. Based on an actuation of the actuating mechanism 106 such as by a push or pull force, the actuating mechanism 106 is capable of causing an actuation in the piercing member 108. This may allow movement of the piercing member 108 between the retracted and the extended position.

In some embodiments, the actuating mechanism 106 may move the piercing member 108 to a completely retracted position such that the piercing member 108 is completely submerged inside the head portion 104. In some other embodiments, the actuating mechanism 106 may move the piercing member 108 to a partially retracted or extended position such that the piercing member 108 partially protrudes out of the head portion 104. In a similar manner, the position of a tip of the piercing member 108 with respect to the head portion 104 may be adjusted from the actuating mechanism 106 based on the requirements. In some embodiments, the actuating mechanism 106 may be configured to incrementally adjust the piercing member 108 with respect to the head portion 104 such that the piercing member 108 can be protruded from the head portion 104 to a defined length or extent. In some other embodiments, the actuating mechanism 106 is configured to adjust the piercing member 108 with respect to the head portion 104 in a discrete manner. In some embodiments, the discrete manner may imply two or binary positions such that the piercing member 108 is either in a completely retracted position or in a completely extended position. In other embodiments, the discrete manner may imply more than two but a fixed number of positions such that by adjusting the actuating mechanism 106 from the knob, the lever and the like to a defined level, a desired position may be reached. In some examples, the desired position may be associated with 25%, 50%, or 75% or any other percentage length of the piercing member 108 coming out of the head portion 104.

In some embodiments, the piercing member 108 of the vaginal manipulator 100 is configured to protrude with respect to the head portion 104 to an extent that it is capable of piercing through a vaginal wall. The bodily implant may be placed over the piercing member 108 in this state. For example, the bodily implant may be placed over the piercing member laproscopically. In other embodiments, another method may be used to place the implant over the piercing member. Therefore, the tip portion of the piercing member 108 may engage with the bodily implant and may temporarily help hold it to the outer surface of the vaginal wall till suturing or any other required process is complete. In some other embodiments, the bodily implant may first be placed laproscopically over a portion of the outer surface of the vaginal wall. The piercing member 108 of the vaginal manipulator 100 is then protruded out with respect to the head portion 104 to an extent that it is capable of piercing through the vaginal wall and the bodily implant.

In accordance with various embodiments, various types of bodily implants available in the market may be utilized. In some embodiments, the bodily implant may include a mesh-based device. For example, the mesh based device may include a Y-shaped mesh, the Y-shaped mesh may include a first arm, a second arm, a third arm, and a support portion. The first arm of the mesh based device is configured to be attached to a first bodily portion and the second arm of the mesh based device is configured to be attached to a second bodily portion. In some embodiments, the first bodily portion is an anterior vaginal wall and the second bodily portion is a posterior vaginal wall of the patient. Therefore, in accordance with these embodiments, the first arm of the mesh based device is attached to the anterior vaginal wall and the second arm of the mesh based device is attached to the posterior vaginal wall. In some embodiments, the first needle may suture and secure the first arm of the mesh based device to the anterior vaginal wall and the second needle may suture and secure the second arm of the mesh based device to the posterior vaginal wall.

In some embodiments, the third arm of the mesh based device is configured to be attached to a third bodily portion. In some embodiments, the third bodily portion is proximate a sacrum of the patient. In some embodiments, the third bodily portion may be a hip bone, a coccyx, a sacrospinous ligament or other tissues. Therefore, in some embodiments, the third arm of the mesh based device is configured to be attached to a tissue proximate the sacrum. In accordance with various embodiments, the implant can have a variety of shapes such as rectangular, square, trapezoidal, and the like. In some embodiments, the support portion is configured to provide a support to a vagina. In accordance with this exemplary type of bodily implant, the piercing member 108 of the vaginal manipulator 100 may engage with mesh structure of the bodily implant and hold it temporarily till the first arm is secured and sutured to the anterior vaginal wall, the second arm is secured and sutured to the posterior vaginal wall, the third arm is secured and sutured to tissues proximate to the sacrum, and the support portion is held properly to provide an adequate support to the vagina.

In certain embodiments, the head portion 104 and the elongated portion 102 form an integral part of the vaginal manipulator 100. In some other embodiments, the elongated portion 102 and the head portion 104 can be removably attached with one another. The head portion 104 can be coupled to the elongated portion 102 through welds, arms, prongs, clips, and other fastening mechanisms.

In some embodiments, the coupling or attachment of the head portion 104 with the elongated portion 102 may not allow relative motion between them. In other embodiments, the elongated member 102 can be coupled to the head portion 104 through a pivot joint such that relative motion between the head portion 104 and the elongated portion 102 is possible. This may assist in manipulation of the bodily tissues and directional adjustments during suturing.

In some embodiments, a suture may be coupled to the piercing member 108 such that the piercing member 108 is capable of moving or placing the suture through a vaginal wall upon actuation by the actuating mechanism 106, when the piercing member 108 is in the extended position. In such cases, the piercing member 108 may be provided a curved shape. The curved piercing member or a needle is configured to protrude out from the head portion 104 in a curvilinear manner. The piercing member 108 may be configured to be moved from the retracted position to a partially extended position and the completely extended position.

Figure 2A:
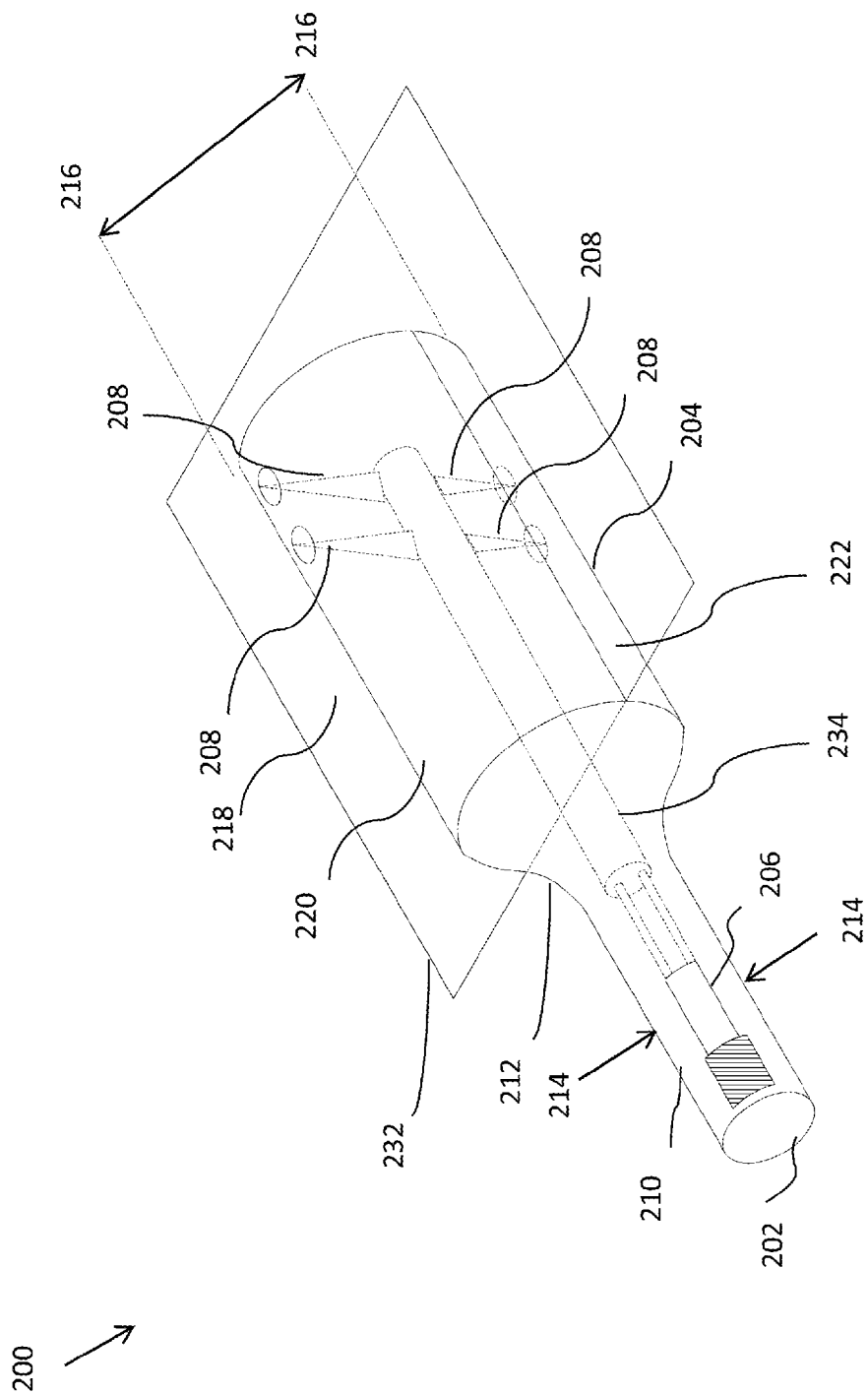
FIG. 2A is a perspective view of a vaginal manipulator in a retracted position, in accordance with an embodiment of the present invention.

FIG. 2A is a perspective view of a vaginal manipulator 200, in accordance with an embodiment of the present invention.

The vaginal manipulator 200 includes an elongated portion 202 and a head portion 204 extending from the elongated portion 202. The head portion 204 further includes a piercing member 208. In accordance with the illustrated embodiment, the piercing member 208 is a linear piercing member 208.

The elongated portion 202 includes a proximal end portion 210 and a distal end portion 212. The elongated portion 202 may have a predefined width referred to as a first width 214. In some embodiments, the elongated portion 202 can be a handle of the vaginal manipulator 200 configured to be held by an operator external from a body tissue. In certain embodiments, the elongated portion 202 may be cylindrical in shape having a circular cross section at the distal end portion 212 and the proximal end portion 210. In other embodiments, the elongated portion 202 may be shaped such that the cross section is rectangular, square, or any other shape at the distal end portion 212 and the proximal end portion 210. As stated above, various other shapes of the elongated portion 202 are possible. For example, the cross section of the proximal end portion 210 and the distal end portion 212 can be rectangular, pentagonal, hexagonal, octal, and the like. As shown in FIG. 2A, the first width 214 of the elongated portion 202 is uniform or substantially uniform from the proximal end portion 210 to the distal end portion 212. In accordance with other embodiments, the elongated portion 202 may be tapered. In some embodiments, the elongated portion 202 is flexible in nature. In other embodiments, the elongated portion 202 is rigid.

The elongated portion 202 further includes an actuating mechanism 206. In various embodiments, the actuating mechanism 206 can include one of a lever, a knob, a slider, a rotator and the like provided on the elongated portion 202 that are discussed below.

The head portion 204 may extend from the distal end portion 212 of the elongated portion 202. As illustrated, the head portion 204 may have a second width 216 such that the second width 216 is greater than the first width 214 (of the elongated portion 202). In accordance with the illustrated embodiment, the head portion 204 projects/bulges laterally from the elongated portion 202 and provides a larger surface area for tissue manipulation and suturing through the head portion 204. In some other embodiments, the first width 214 of the elongated member 202 and the second width 216 of the head portion 204 may be same or substantially same.

In accordance with the illustrated embodiments of FIG. 2A, the head portion may have a tubular surface 218. As shown in FIG. 2A, the tubular surface of the head portion 204 may be assumed to be divided into two halves—an upper half representing a top surface or a first surface 220, and a lower half representing a bottom surface or a second surface 222. An imaginary plane 232 passing along the head portion 204 and cutting it into the two halves is depicted for the purpose of simplicity of description.

In some other embodiments, a head portion such as the head portion 304 may include a flat surface as shown in FIG. 3A and FIG. 3B. In accordance with these embodiments, the head portion 304 may include a first surface 320 on an outer side (top side) of the head portion 304 as shown in FIG. 3A and a second surface 322 on an inner side (bottom side) as shown in FIG. 3B opposite the first surface 320. In some embodiments, one or both of the first surface 320 and the second surface 322 may be flat (as shown in FIGS. 3A and 3B), or any other shape.

In some embodiments, the surgeon/operator may use the first surface 220 to suture anterior portions of a vagina and the second surface 222 to suture posterior portions of the vagina. In some embodiments, one or both of the first surface 220 and the second surface 222 may be tubular in shape.

Figure 2B:
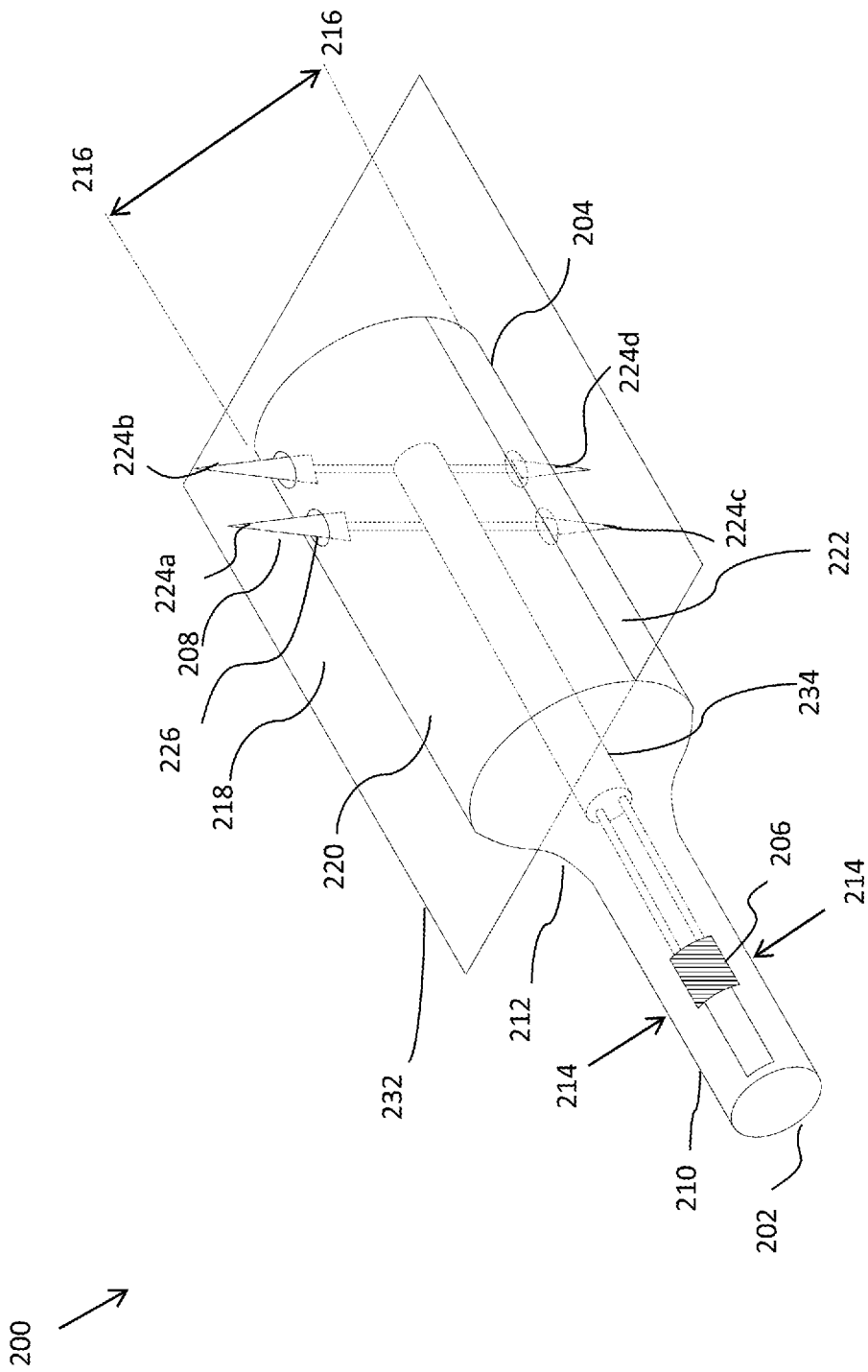
FIG. 2B is a perspective view of the vaginal manipulator of FIG. 2A, in an extended configuration.
Figure 2C:
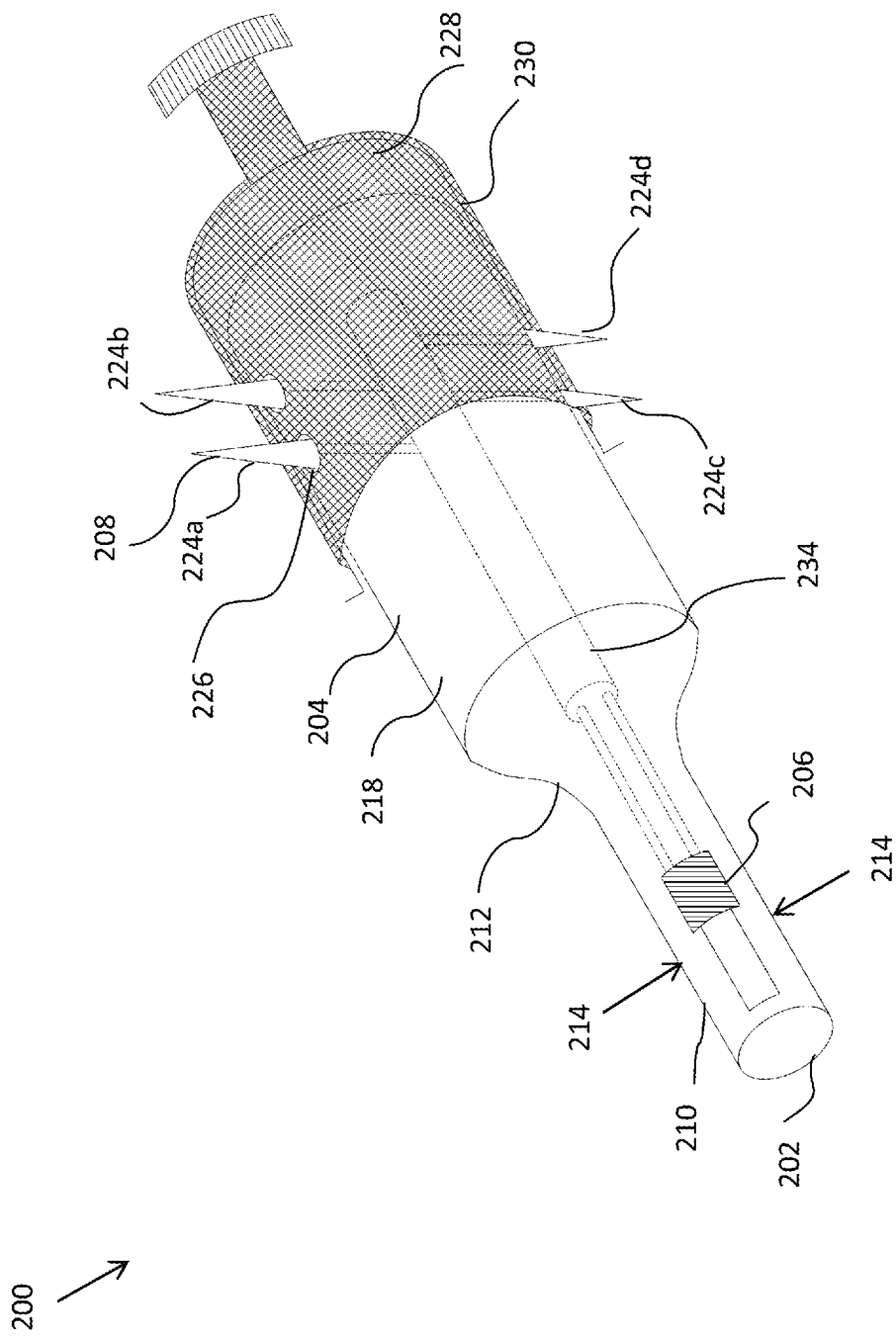
FIG. 2C is a perspective view of the vaginal manipulator of FIG. 2A engaged with a bodily implant, in accordance with an embodiment of the present invention.

The head portion 204 further includes a piercing member 208. In accordance with the illustrated embodiment, the piercing member 208 is a linear piercing member 208 as discussed above. The piercing member 208 is configured to temporarily help retain a bodily implant 228 (as shown in FIG. 2C) proximate an outer surface of a vaginal wall 230 (as shown in FIG. 2C). The piercing member 208 is configured to move from a refracted position to an extended position with respect to the head portion 204.

In some embodiments, the piercing member 208 is disposed and fitted within the head portion 204 of the vaginal manipulator 200 such that the piercing member 208 may move from a location internal to the head portion 204 to a location external to the head portion 204 and toward the first surface 220. The head portion 204 may include a hole that defines a lumen 226 (as shown in FIG. 2B) such that the piercing member 208 may be extended through the lumen 226. In some embodiments, the piercing member 208 is disposed and fitted within the Head portion 204 of the vaginal manipulator 200 such that the piercing member 208 may move from a location internal to the head portion 204 to a location external to the head portion 204 and toward the second surface 222.

In some embodiments, the piercing member 208 may be or further includes a needle such that the needle is configured to extend from internal to the head portion 204 and toward respective surfaces such as the first surface 220 and the second surface 222 and past the first surface 220 and the second surface 222. The needle that extends toward the first surface 220 can be termed as a first needle and the needle that extends toward the second surface 222 can be termed as a second needle. The first surface 220 and the second surface 222 are disposed or face substantially opposite to one another and so tip portions of the first needle and the second needle face opposite one another.

As illustrated in FIG. 2A, the head portion 204 includes the piercing member 208. The piercing member 208 has four needles 224a, 224b, 224c, and 224d (referred to as 224 together). The needles 224 are shown in the retracted position in FIG. 2A. In the retracted position, the needles 224 are completely inside the head portion 204 and are not exposed beyond a boundary of the first surface 220 or the second surface 222. In some embodiments, the head portion 204 may include four holes that define lumens 226 to receive the needles 224. In the retracted position, the four needles 224a, 224b, 224c, 224d enter into the respective lumens 226 completely or substantially. The lumens 226 are provided in a defined layout in the illustrated embodiment. Two lumens are provided on the first surface 220 while other two lumens are provided at the second surface 222. In several other embodiments, however, the layout of the lumens 226 and disposition of the needles 224 may vary. Further, in some embodiments, the number of needles 224 provided on the head portion 204 may vary based on the requirements. For example, as illustrated, the vaginal manipulator 200 and the piercing member 208 are capable of facilitating holding of a bodily implant 228 at four locations. The number of needles 224 may be increased thereby increasing holding force when the needles 224 engage with the bodily implant 228. In some embodiments, the number of needles 224 can be decreased to one on each side or merely one over the head portion 204. This may decrease the holding force when the needles 224 engage with the bodily implant 228. Further, the spacing between various needles 224 placed at distinct locations may vary based on the design requirements. This may define holding force distribution along the bodily implant 228 when the needles 224 engage with the bodily implant 228.

The extended position of the piercing member 208 is shown in FIG. 2B, which illustrates a perspective view of the vaginal manipulator 200 with the piercing member 208 in the extended position. In accordance with some embodiments, the piercing member 208 is configured to protrude with respect to the head portion 204, (when in the extended position), and pierce through the vaginal wall 230 (when positioned inside the body). In the extended position, a substantial length of the piercing member 208 comes out of the head portion 204. For example, the tip portion of the piercing member 208 may come out of the head portion 204 to a defined extent or length.

The piercing member 208 can be moved from the retracted position to the extended position as described above with the use of the actuating mechanism 206 provided on the elongated portion 202. The actuating mechanism 206 is configured to move the piercing member 208 from its retracted position to its extended position.

In some embodiments, the actuating mechanism 206 may include one of a lever and a knob, a slider, a rotator and the like. The actuating mechanism 206 can be operatively coupled to the piercing member 208 and can be configured to move the piercing member 208 between the retracted position and the extended position. For example, the actuating mechanism 206 may move the piercing member 208 to a completely retracted position such that the piercing member 208 is completely submerged inside the head portion 204 as illustrated in FIG. 2A. In some other embodiments, the actuating mechanism 206 may move the piercing member 208 to a partially retracted or extended position such that the piercing member 208 partially protrudes from the head portion 204. In similar manner, the position of the piercing member 208 may be adjusted from the actuating mechanism 206 based on the requirements. In some embodiments, the actuating mechanism 206 may be configured to incrementally adjust the piercing member 208 with respect to the head portion 204 such that the piercing member 208 can be protruded from the head portion 204 to a defined length or extend as illustrated in FIG. 2B. In some other embodiments, the actuating mechanism 206 is configured to adjust the piercing member 208 with respect to the head portion 204 in a discrete manner. In some embodiments, the discrete manner may imply two or binary positions such that the piercing member 208 is either in a completely retracted state as shown in FIG. 2A or in a completely extended position as shown below in FIG. 2B. In other embodiments, the discrete manner may imply more than two but fixed numbers of positions such that by adjusting the actuating mechanism 206 from the knob, the lever and the like elements to a defined level, a desired position may be reached. In some examples, the desired position may be associated with 25%, 50%, or 75% or any other percentage length of the piercing member 208 coming out of the head portion 204. In other embodiments, the device may define a lumen through which a medical practitioner may insert a needle. In such embodiments, the lumen can communicate with an opening at the distal end of the device such that the needle inserted by the medial practitioner may pierce vaginal tissue when it exits or extends from the lumen.

Various types of actuating mechanisms 206 may be deployed that can be configured to move the piercing member 208 between the retracted position and the extended position. For example, in some embodiments, the piercing member 208 can be slidably actuated to move between the extended and the refracted positions. In such cases, springs and various other linkages that are configured to cause a slidable movement may be used in the actuating mechanism 206. In some embodiments, linkages such as including a tubular member 234 as shown in FIG. 2A may be used to slidably actuate the piercing member 208 to move between the extended and the retracted position. Similarly, various other types of actuating mechanisms 206 may also be used. The actuating mechanism 206 can also include one of a lever, a knob, a slider, a rotator and the like for causing an actuation of the piercing member 208.

In some embodiments, the actuating mechanism 206 is operatively coupled to the piercing member 208. For example, the head portion 204 and the elongated portion 202 may include a lumen such that the actuating mechanism 206 or a portion of the actuating mechanism 206 is disposed within the lumen. The actuating mechanism 206 extends through at least a portion of length of the lumen and gets operatively coupled to the piercing member 208 disposed within the head portion 204. Based on an actuation of the actuating mechanism 206 such as by a push or pull force, the actuating mechanism 206 is capable of causing an actuation in the piercing member 208. This may allow movement of the piercing member 208 between the retracted and the extended position.

In accordance with various embodiments, various types of bodily implants available in the market may be utilized. In some embodiments, the bodily implant 228 may include a mesh based device. For example, the mesh based device may include a Y-shaped mesh. The Y-shaped mesh may include a first arm, a second arm, a third arm, and a support portion. The first arm of the mesh based device is configured to be attached to a first bodily portion and the second arm of the mesh based device is configured to be attached to a second bodily portion. In some embodiments, the first bodily portion is an anterior vaginal wall and the second bodily portion is a posterior vaginal wall of the patient. Therefore, in accordance with these embodiments, the first arm of the mesh based device can be attached to the anterior vaginal wall using the first surface 220 of the head portion 204 and the second arm of the mesh based device can be attached to the posterior vaginal wall using the second surface 222 of the head portion 204. In some embodiments, the third arm of the mesh based device is configured to be attached to a third bodily portion. In some embodiments, the third bodily portion is a sacrum of the patient. Therefore, in some embodiments, the third arm of the mesh based device is configured to be attached to proximate the sacrum. In accordance with various embodiments, the implant can have a variety of shapes such as rectangular, square, trapezoidal, and the like. In some embodiments, the support portion is configured to provide a support to a vagina. In accordance with this exemplary type of bodily implant 228, the piercing member 208 of the vaginal manipulator 200 may engage the mesh structure of the bodily implant 228 and help hold it temporarily till the first arm is secured and sutured to the anterior vaginal wall, the second arm is secured and sutured to the posterior vaginal wall, the third arm is secured and sutured to tissues proximate the sacrum, and the support portion is held properly to provide an adequate support to the vagina. In some embodiments, the first needle may help suture and secure the first arm of the mesh based device to the anterior vaginal wall and the second needle may help suture and secure the second arm of the mesh based device to the posterior vaginal wall.

In certain embodiments, the head portion 204 and the elongated portion 202 may form an integral part of the vaginal manipulator 200. In some other embodiments, the elongated portion 202 and the head portion 204 can be removably attached with one another. The head portion 204 can be coupled to the elongated portion 202 through welds, arms, prongs, clips, and other fastening mechanisms.

In some embodiments, the coupling/attachment of the head portion 204 with the elongated portion 202 may not allow relative motion between them. In other embodiments, the elongated member 202 can be coupled to the head portion 204 through a pivot joint such that relative motion between the head portion 204 and the elongated portion 202 is possible. This may assist in manipulation of the bodily tissues and directional adjustments during suturing or any other required process.

In certain embodiments, the handle may form an integral part of the vaginal manipulator 200. In some other embodiments, the handle can be removably attached with one another. The handle can be coupled to the elongated portion 202 through welds, arms, prongs, clips, and other fastening mechanisms.

FIG. 2C is a perspective view of the vaginal manipulator 200 and engaged with the bodily implant 228 in the extended position, in accordance with an embodiment of the present invention. In the extended position, a substantial length of the piercing member 208 comes out of the head portion 204. For example, the tip portion of the piercing member 208 may come out of the head portion 204 to a defined extent or length that depends on an amount of adjustment made by the actuating mechanism 206.

The piercing member 208 of the vaginal manipulator 200 is configured to protrude with respect to the head portion 204 to an extent that it is capable of piercing through a vaginal wall 230. The bodily implant 228 such as a mesh and sling may be placed laproscopically over the piercing member 208 in this state. Therefore, the tip portion of the piercing member 208 may engage with the bodily implant 228 and may temporarily help hold it to the outer surface of the vaginal wall 230 till the suturing or any other required process is complete. In some other embodiments, the bodily implant 228 may first be placed laproscopically over a portion of the outer surface of the vaginal wall 230. The piercing member 208 of the vaginal manipulator 200 is then protruded out with respect to the head portion 204 to an extent that it is capable of piercing through the vaginal wall 230 and through the bodily implant 228. In some embodiments, the bodily implant 228 is made from one of a polypropylene and a biologic material.

As illustrated in FIG. 2C, the bodily implant 228 is a mesh-based device which is overlaid over the piercing member 208 to help hold the bodily implant 228 in place till the suturing or any other required process is complete. As shown, the piercing member 208 is in the extended position, and the piercing member 208 protrudes with respect to the head portion 204.

In accordance with various embodiments, various types of bodily implants as discussed above may be used.

In accordance with some of the embodiments, the head portion 204 may be of a tubular shape 218 as described above. In some other embodiments, the head portion such as the head portion 304 may have flat surfaces 318 as shown in FIG. 3A and FIG. 3B. FIGS. 3A and 3B illustrate a vaginal manipulator 300 in accordance with an embodiment of the present invention. The vaginal manipulator 300 includes a head portion 304 and an elongated portion 302. The elongated portion 302 includes a proximal end portion 310 and a distal end portion 312. The elongated portion 302 may have a predefined width referred to as a first width 314. In some embodiments, the elongated portion 302 can be a handle of the vaginal manipulator 300 configured to be held by an operator external from a body tissue. The elongated portion 302 further includes an actuating mechanism 306. In various embodiments, the actuating mechanism 306 can include one of a lever, a knob, a slider, a rotator and the like provided on the elongated portion 302 that are discussed above in conjunction with FIG. 2A. The head portion 304 may extend from the distal end portion 312 of the elongated portion 302. As illustrated, the head portion 304 may have a second width 316 such that the second width 316 is greater than the first width 314 (of the elongated portion 302). In some embodiments, the head portion 304 may include a first flat surface 320 on an outer side of the head portion 304 as shown in FIG. 3A and a second flat surface 322 on an inner side as shown in FIG. 3B, opposite the first flat surface 320. In some embodiments, the surgeon/operator may use the first flat surface 320 to suture on anterior portions of the vagina and the second flat surface 322 to suture on posterior portions of the vagina. In some embodiments, one or both of the first flat surface 320 and the second flat surface 322 may not be substantially flat.

The head portion 304 can further include a piercing member 308. In accordance with some embodiments, the piercing member 308 is a linear piercing member 308. The piercing member 308 is configured to move from a retracted position to an extended position with respect to the head portion 304.

In some embodiments, the piercing member 308 is disposed and fitted within the head portion 304 of the vaginal manipulator 300 such that the piercing member 308 may move from a location internal to the head portion 304 to a location external to the head portion 304 and toward the first surface 320. The head portion 304 may include a hole that defines a lumen 326 (as shown in FIGS. 3A and 3B) such that the piercing member 308 may be extended through the lumen 326. In some embodiments, the piercing member 308 is disposed and fitted within the head portion 304 of the vaginal manipulator 300 such that the piercing member 308 may move from a location internal to the head portion 304 to a location external to the head portion 304 and toward the second surface 322.

Figure 4A:
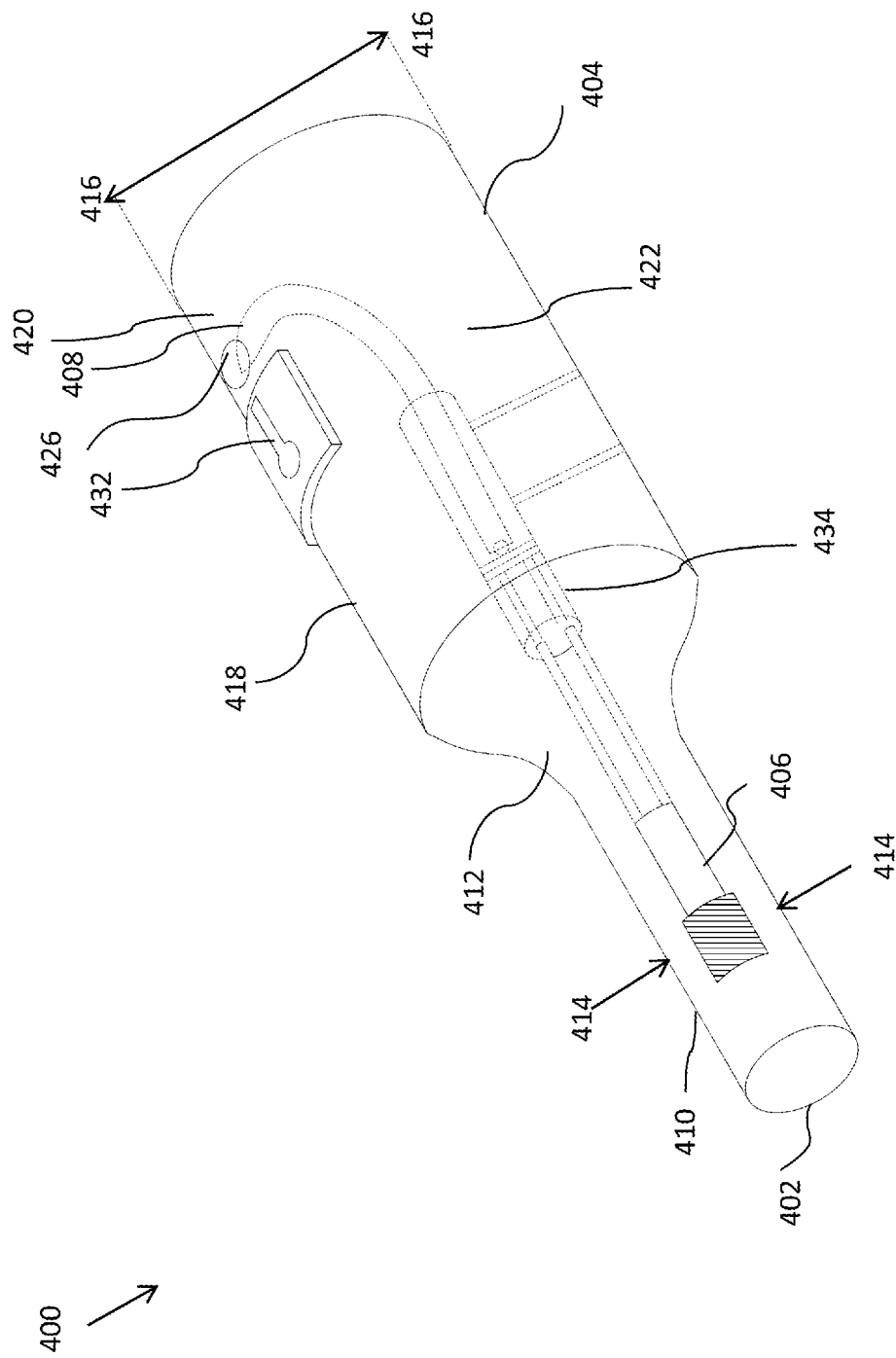
FIG. 4A is a perspective view of a vaginal manipulator in a retracted position, in accordance with an embodiment of the present invention.
Figure 4B:
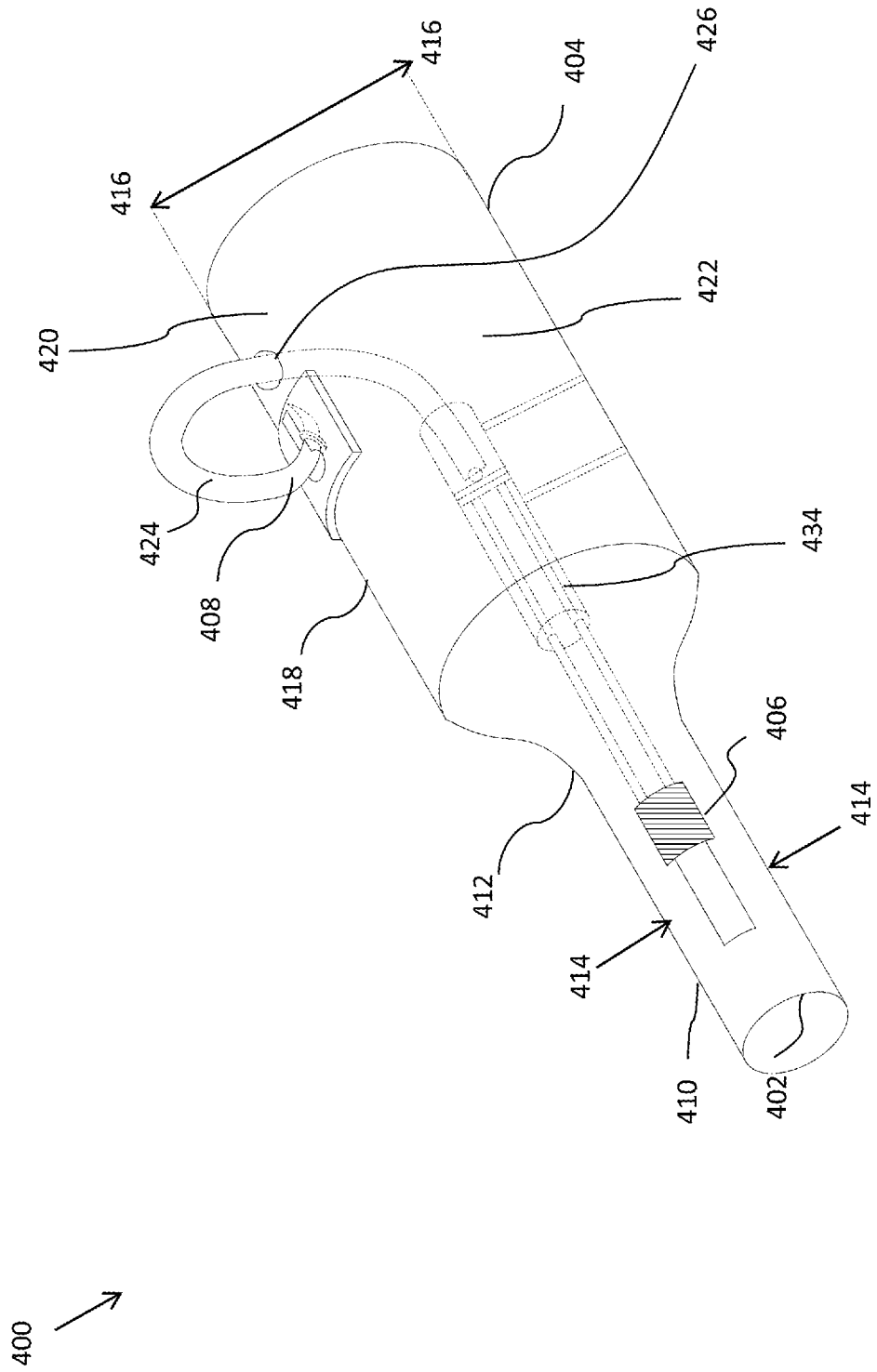
FIG. 4B is a perspective view of the vaginal manipulator of FIG. 4A, in a completely extended position, in accordance with an embodiment of the present invention.

FIG. 4A is a perspective view of a vaginal manipulator 400 in a retracted position, in accordance with an embodiment of the present invention. The vaginal manipulator 400 includes an elongated portion 402 and a head portion 404 extending from the elongated portion 402 in a retracted position. The head portion 404 further includes a piercing member 408. The piercing member 408 has one needle 424 as shown in FIG. 4B. In some other embodiments, the piercing member 408 can include more than one needle. In accordance with some embodiments, the head portion 404 and the elongated portion 402 may be similar to the head portion and the elongated portion as described above with respect to other embodiments.

In accordance with the embodiments illustrated in FIG. 4A, the vaginal manipulator 400 includes a piercing member 408 with a curved shape. The piercing member 408 that can be a curved piercing member 408 is configured to be submerged within the head portion 404 in the retracted position as illustrated in FIG. 4A.

The elongated portion 402 includes a proximal end portion 410 and a distal end portion 412. The elongated portion 402 may have a predefined width referred to as a first width 414. In some embodiments, the elongated portion 402 can be a handle of the vaginal manipulator 400 configured to be held by an operator external from a body tissue.

The head portion 404 extends from the distal end portion 412 of the elongated portion 402. As illustrated, the head portion 404 may have a second width 416 such that the second width 416 is greater than the first width 414 (of the elongated portion 402). In some other embodiments, the first width 414 of the elongated member 402 and the second width 416 of the head portion 404 may be same or substantially same. In some embodiments, the head portion 404 may have a tubular surface 418. In some other embodiments, the head portion 404 may be circular, cylindrical, flat or of any other shape.

The head portion 404 further includes the curved piercing member 408 as mentioned above. The curved piercing member 408 is configured to pierce through the vaginal wall 430 (as shown in FIG. 3D) such that a tip portion of the curved piercing member 408 passes through a bodily implant 428 (as shown in FIG. 3D) placed to an outer surface of the vaginal wall 430 and affix the bodily implant 428. In certain embodiments, the piercing member 408 can be a surgical needle configured to pierce through the patient's body during insertion. The surgical needle may be made of a metal such as stainless steel.

The head portion 404 may include a first surface 420 on an outer side of the head portion 404 and a second surface 422 on an inner side opposite the first surface 420. The first surface 420 and the second surface 422 are configured to provide a larger surface area for manipulation of bodily tissues such as vaginal tissues and for suturing facilitation. In some embodiments, the piercing member 408 is disposed and fitted within the head portion 404 of the vaginal manipulator 400 such that the piercing member 408 may move from a location internal to the head portion 404 to a location external to the head portion 404 and toward the first surface 420. The head portion 404 may include a hole that defines a lumen 426 such that the piercing member 408 may be extended through the lumen 426. In some embodiments, the piercing member 408 is disposed and fitted within the head portion 404 of the vaginal manipulator 400 such that the piercing member 408 may move from a location internal to the head portion 404 to a location external to the head portion 404 and toward the second surface 422.

The piercing member 408 is configured to move from a retracted position to an extended position (shown in FIGS. 4A and 4B) with respect to the head portion 404. An actuating mechanism 406 provided on the elongated portion 402 is configured to move the piercing member 408 from its retracted position to its extended position. In some embodiments, the actuating mechanism 406 can include a tubular member 434 that can be operatively coupled to the piercing member 408. The tubular member 434 may also be coupled to or includes various other mechanical linkages configured to actuate or assist in actuation of the piercing member 408. In some embodiments, the actuating mechanism 406 can include one of a lever and a knob, a slider, a rotator and the like elements that are configured to move the piercing member 408 from external to a body tissue and move the piercing member 408 from the retracted position to the extended position. The piercing member 408 can be a curved needle as shown in FIG. 4B such that is configured to protrude with respect to head portion 404, when in the extended position, and pierce through the vaginal wall 430 (as shown in FIG. 4D). The head portion 404 including the piercing member 408 is configured to help hold a bodily implant 428 to an outer surface of the vaginal wall 430 for suturing. The piercing member 408 is configured to protrude from the head portion 404 in a curvilinear manner. The curved piercing member 408 is configured to pierce through the vaginal wall 430 such that a tip portion of the curved needle passes through the bodily implant 428 placed to the outer surface of the vaginal wall 430 and affix the bodily implant 428.

In some embodiments, the suture may be coupled to a piercing member 408 before or after insertion and placement of the vaginal manipulator 400 into the patient's body. The piercing member 408 is configured to move the suture through the vaginal wall 430 when the piercing member 408 is in its extended position. This may cause affixing the bodily implant 428 to the outer surface of the vaginal wall 430.

In some embodiments, the vaginal manipulator 400 may further include a needle catch 432 disposed on the head portion 404. The needle catch 432 is configured to receive the piercing member 408 such as the curved needle. A user (such as a physician or other medical personnel) may actuate the actuating mechanism 406 (such as the lever, the knob, the slider, the rotator and the like elements) provided on the elongate member 402. The user continues to actuate the actuating mechanism 406 until the curved needle enters the needle catch 432 to move the suture 436 to secure the bodily implant 428 to the outer surface of the vaginal wall 430 when the piercing member 408 is in the extended position. The piercing member 408 is configured to enter the needle catch 432 (when the piercing member 408 is in the extended position as shown in FIG. 4B).

Figure 4C:
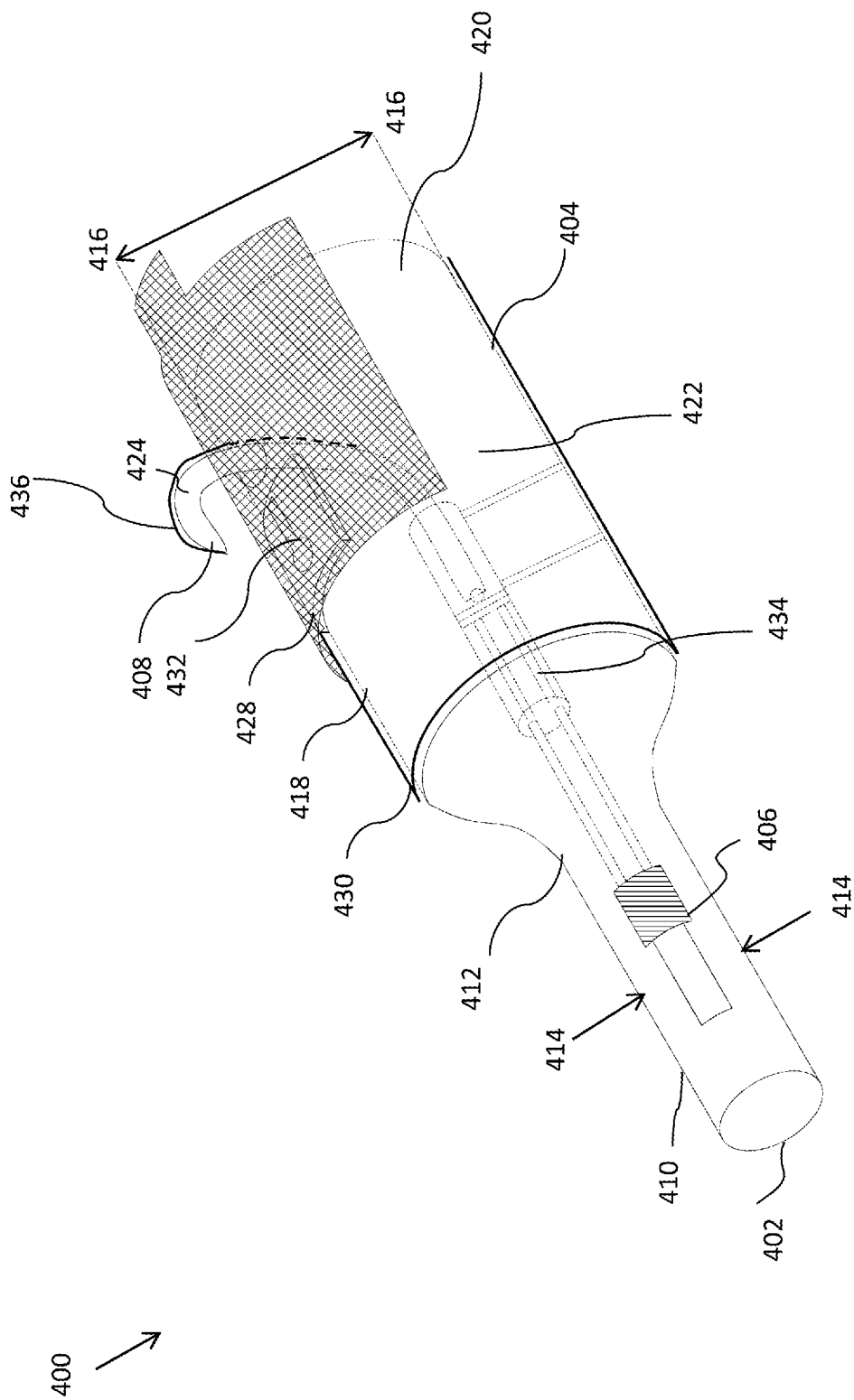
FIG. 4C is a perspective view of the vaginal manipulator of FIG. 4A, in a partially extended position, in accordance with an embodiment of the present invention.
Figure 4D:
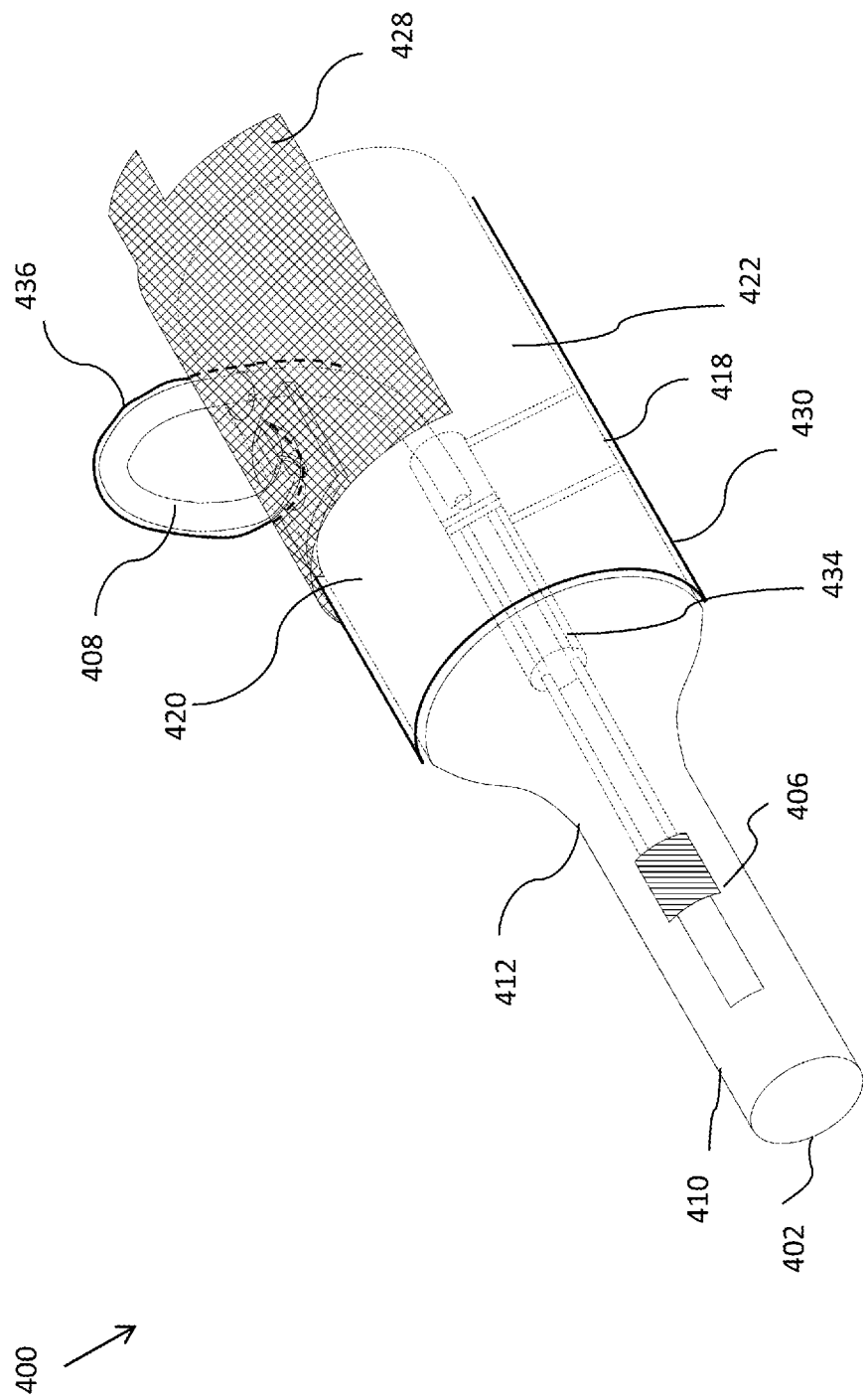
FIG. 4D is a perspective view of the vaginal manipulator of FIG. 4A, and engaged with a bodily implant, in accordance with an embodiment of the present invention.

The piercing member 408 is loaded with a suture 436 (when the piercing member 408 is in the extended position as shown in FIG. 4C). In some embodiments, the suture 436 is coupled to the piercing member before insertion and placement of the vaginal manipulator 400 into the patient's body. In some embodiments, the suture 436 is coupled to the piercing member after insertion and placement of the vaginal manipulator 400 into the patient's body.

Figure 4E:
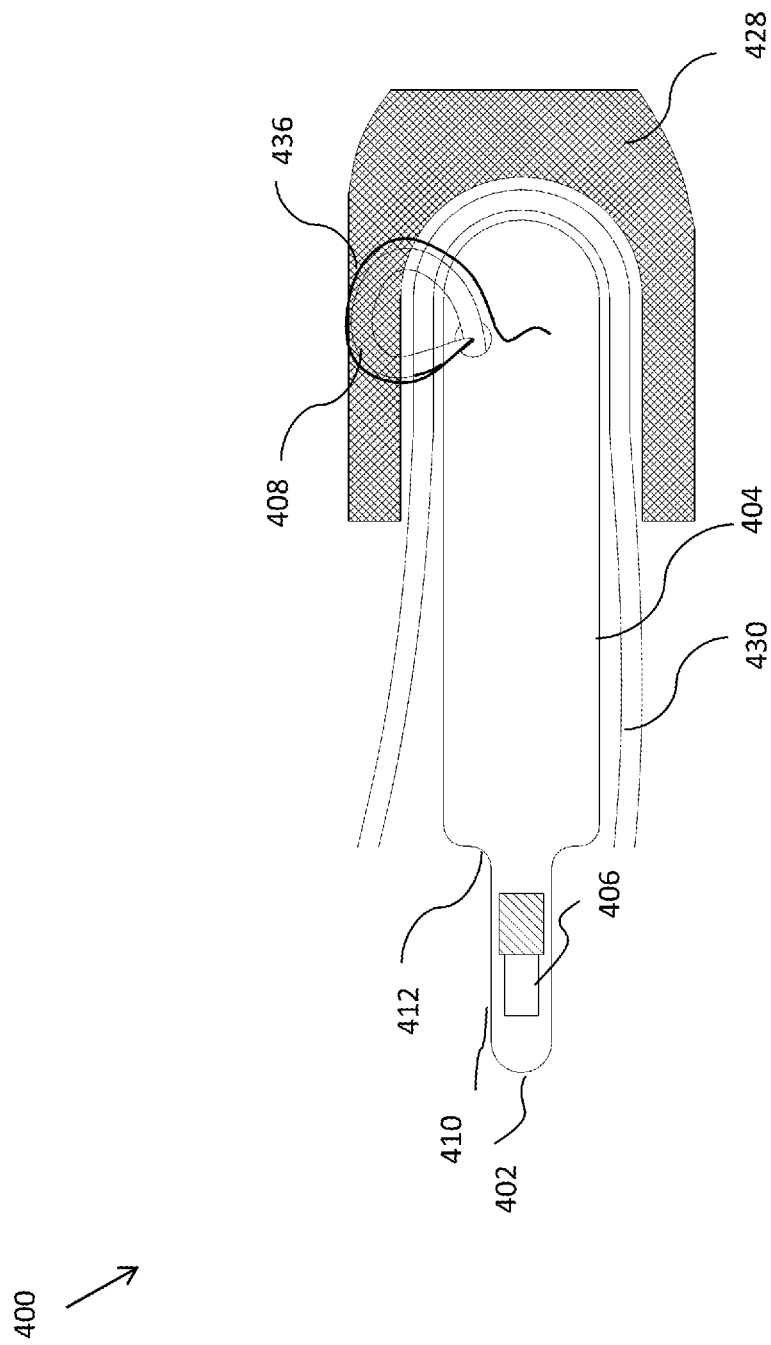
FIG. 4E illustrates the vaginal manipulator of FIG. 4D, and engaged with the bodily implant, in a different view.

The suture 436 (coupled to the piercing member 408) passes through the bodily implant and moves toward the needle catch 232 as the piercing member moves from the retracted position to the extended position. The detailed mechanism for the same is elaborated below. The piercing member 408 is brought to the extended position with respect to the head portion 404, such that the suture 436 traverses a path from the outer surface of the vaginal wall 430 to the inner surface of the vaginal wall (as shown in FIG. 4D). FIG. 4E illustrates a different orientation of the vaginal manipulator of FIG. 4D.

The actuating mechanism 406 is configured to move the piercing member 408 from its retracted position to its extended position. In the extended position, the piercing member 408 is configured to move the suture 436 through the vaginal wall 430 so that the suture 436 is captured by the needle catch 432. Subsequently, after the suture 436 is moved through the vaginal wall 430, the piercing member 408 can be brought to the retracted position and the vaginal manipulator 400 can be moved out of the body. The suture 436 can then be fixed or tied to bodily tissues. This may cause affixing the bodily implant 428 to the outer surface of the vaginal wall 430.

Figure 4F:
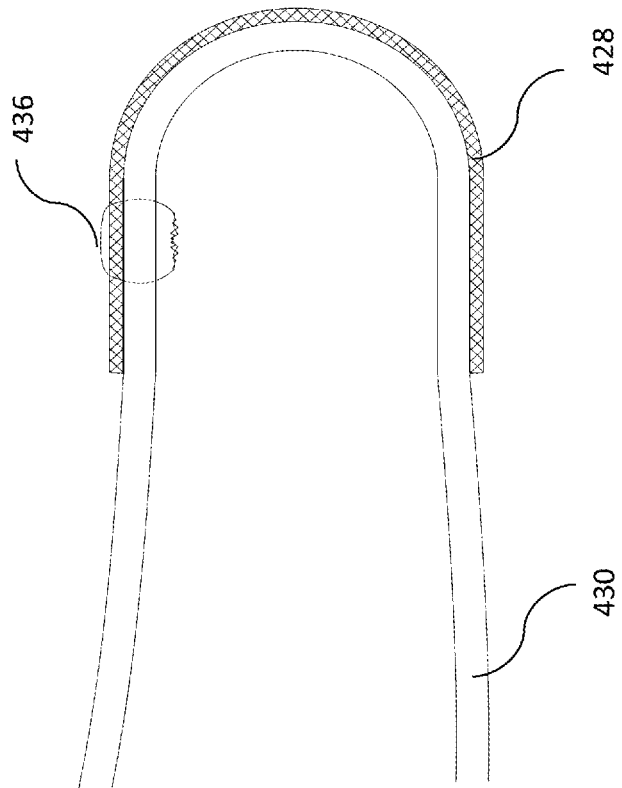
FIG. 4F illustrates an enlarged view of a suture knotted to a vaginal wall of a patient with the use of a vaginal manipulator.

In some embodiments, the vaginal manipulator 400 is configured to be inserted into the body (contacting an inner surface of the vaginal wall) in the retracted position. The vaginal manipulator 400 is then moved to a partially extended position (as shown in FIG. 4C) where the piercing member 408 extends or protrudes out of the head portion 404 and pierces through the vaginal wall 430. The bodily implant 428 can then be placed over the piercing member 408 on an outer surface of the vaginal wall 430 in such a manner that the piercing member 408 engages with the bodily implant 428. At this state, the suture 436 is coupled to the piercing member 408. The piercing member 408 is then brought to the retracted position such that the suture 436 traverses a path from the outer surface of the vaginal wall 430 to the inner surface of the vaginal wall. The suture 436 can then be tied as shown in FIG. 4F. In this embodiment, the suture 436 crosses or pierces through the vaginal wall 430 once while going from the inner surface of the vaginal wall to the outer surface of the vaginal wall 430. And, thus, a suture 436 is placed to affix the bodily implant 428 on the outer surface. Simultaneously, the vaginal manipulator 400 also assists in holding the bodily implant 428 temporarily by providing a support through frictional resistance provided by engagement of the piercing member 408 with the mesh temporarily till the piercing member 408 places the suture 436 and secures it firmly. Subsequently the bodily implant 428 is still held at its location even when the temporary force (due to engagement) is withdrawn by removing the vaginal manipulator 400.

In some other embodiments, the suture 436 can be coupled to the piercing member 408 before insertion into the body. The subsequent steps are similar as above except that when the piercing member 408 is brought to the partially extended position, the piercing member 408 traverses from the inner surface of the vaginal wall to the outer surface of the vaginal wall with the suture 436 piercing through the vaginal wall 430. And, when the piercing member 408 is moved to the completely extended position (as shown in FIG. 4B), the piercing member 408 further extends in a manner that due to the curved nature of the piercing member 408, the tip portion of the piercing member 408 reaches proximate a proximal portion of the piercing member 408. In this manner, the suture 436 traverses a path back from the outer surface of the vaginal wall 430 to the inner surface of the vaginal wall. The traversed path is different than while moving the piercing member 408 from the inner surface to the outer surface of the vaginal wall 430. The suture 436 can then be tied. In this embodiment, the suture 436 traverses a substantially cyclic path and can help tie the bodily implant 428 in a better and more secured way. In some embodiments, the sutures placed in this manner are configured to permanently hold or help hold the implant in place. In other embodiments, the sutures placed in this matter are configured to temporarily hold the implant in place within the body of the patient. In such embodiments, a medical practitioner may suture the implant in place using standard techniques to permanently fix or couple the implant to the bodily tissue.

FIG. 4B is a perspective view of the vaginal manipulator 400 in the completely extended position as discussed above.

FIG. 4C is a top view of the vaginal manipulator 400 in the partially extended position as discussed above. The bodily implant 428 as mentioned above can be made from one of a polypropylene and a biologic material, in some embodiments. The bodily implant 428 has been described in conjunction with FIG. 2C above.

An enlarged view of the bodily implant 428 which is held to the outer surface of the vaginal wall 430 is illustrated in FIG. 4D. As illustrated, the bodily implant 428 is a mesh-based device which is laid over the piercing member 408 to hold the bodily implant 428 in place while suturing. The piercing member 408 is in the completely extended position with respect to the head portion 404 such that the piercing member 408 traverses from the inner surface to the outer surface and then back from the outer surface to the inner surface.

An enlarged view of the bodily implant 428 which is held to the outer surface of the vaginal wall 430 is illustrated in FIG. 4E. FIG. 4E illustrates a different orientation of the vaginal manipulator of FIG. 4D. FIG. 4F illustrates an enlarged view of the bodily implant secured to the vagina.

Figure 5A:
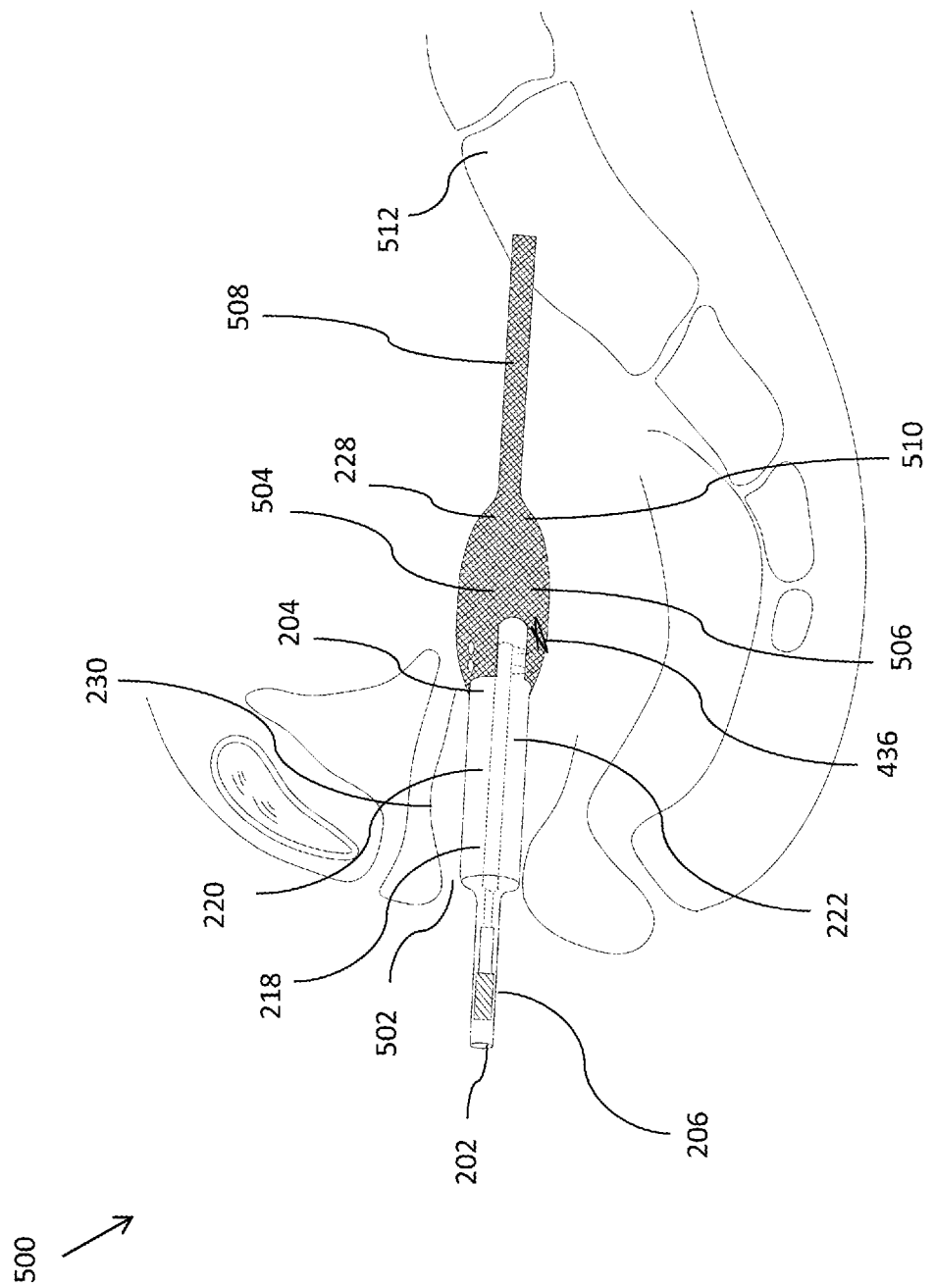
FIG. 5A illustrates placement of a vaginal manipulator in a retracted position inside a vagina, in accordance with an embodiment of the present invention.

FIG. 5A illustrates placement of the bodily implant 228 inside a vagina 502 for manipulation of bodily tissues and suturing of the bodily implant 228 to a bodily tissue. The vaginal manipulator 200 is hereafter used to illustrate and describe some embodiments. The piercing member 208 is shown in the retracted position in FIG. 5A. The head portion 204 of the vaginal manipulator 200 and the piercing member 208 may assist in the suturing process. It may also act as a backstop for suturing during abdominal/laparoscopic pelvic floor procedures. In some embodiments, the bodily implant 228 includes a Y shaped mesh device with a first arm 504, a second arm 506, a third arm 508 and a support portion 510. The support portion 510 is configured to provide support to the vagina 502. The first arm 504 and the second arm 506 are configured to be respectively attached to an anterior and a posterior portion of the vaginal wall 230 and the third arm 508 is configured to be attached to a sacrum 512 of a patient.

Figure 5B:
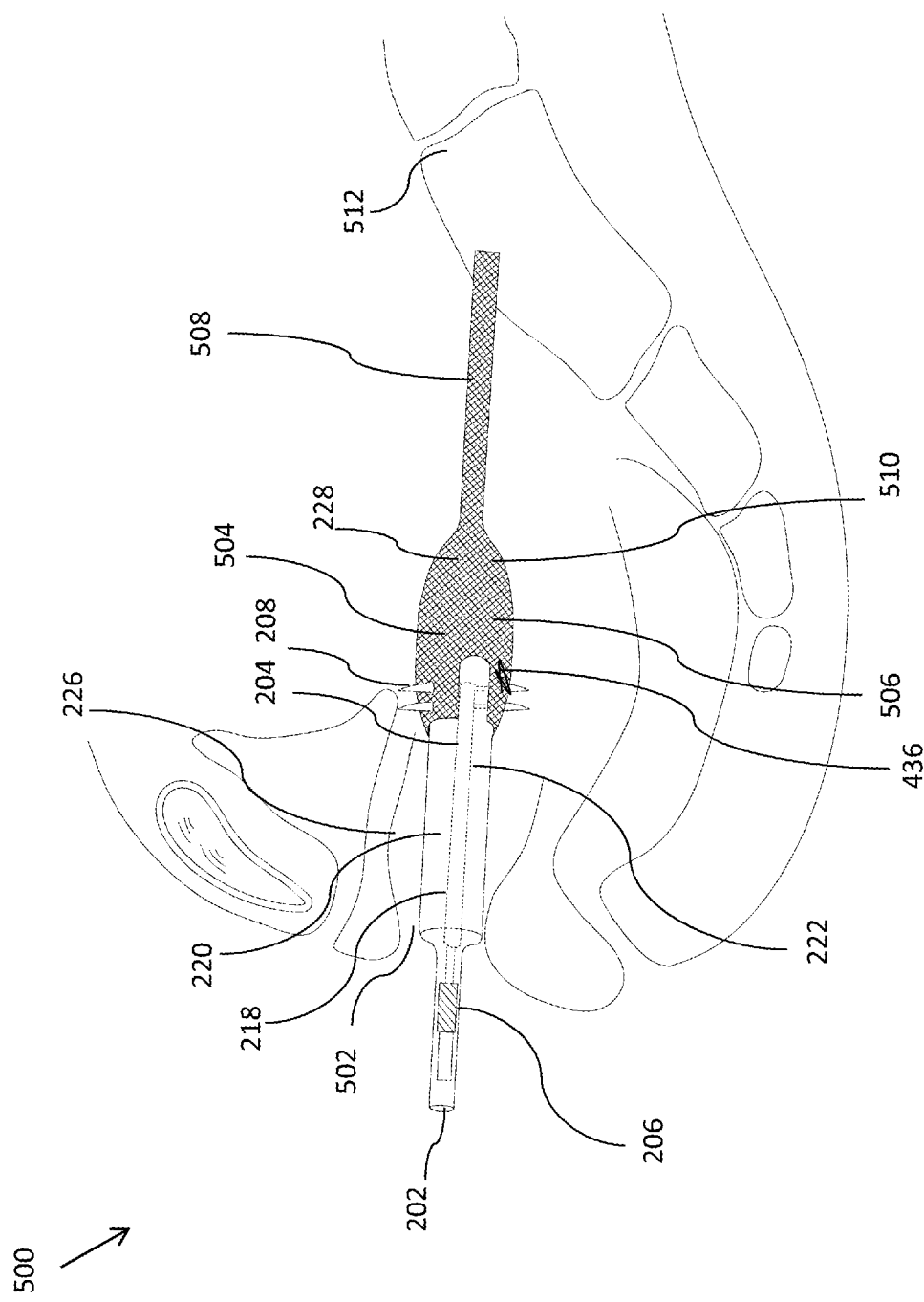
FIG. 5B illustrates placement of a vaginal manipulator in an extended position inside a vagina, in accordance with an embodiment of the present invention.

FIG. 5B illustrates placement of the bodily implant 228 inside the vagina 502 for manipulation of bodily tissues and suturing of the bodily implant 228 to a bodily tissue. The piercing member 208 is shown in the extended position in FIG. 5B. The bodily implant 228, as discussed above, is configured to be placed laparoscopically over the piercing member 208, when the piercing member 208 is in the extended position, and extending through the outer surface of the vaginal wall 230 such that the bodily implant 222 is temporarily held to the outer surface of the vaginal wall 230 by the vaginal manipulator 200. In some other embodiments, the bodily implant 228 can first be placed laparoscopically over a portion of the outer surface of the vaginal wall 230. The piercing member 208 of the vaginal manipulator 200 is then protruded out with respect to the head portion 204 to an extent that it is capable of piercing through the vaginal wall 230 over the bodily implant 228.

Figure 6:
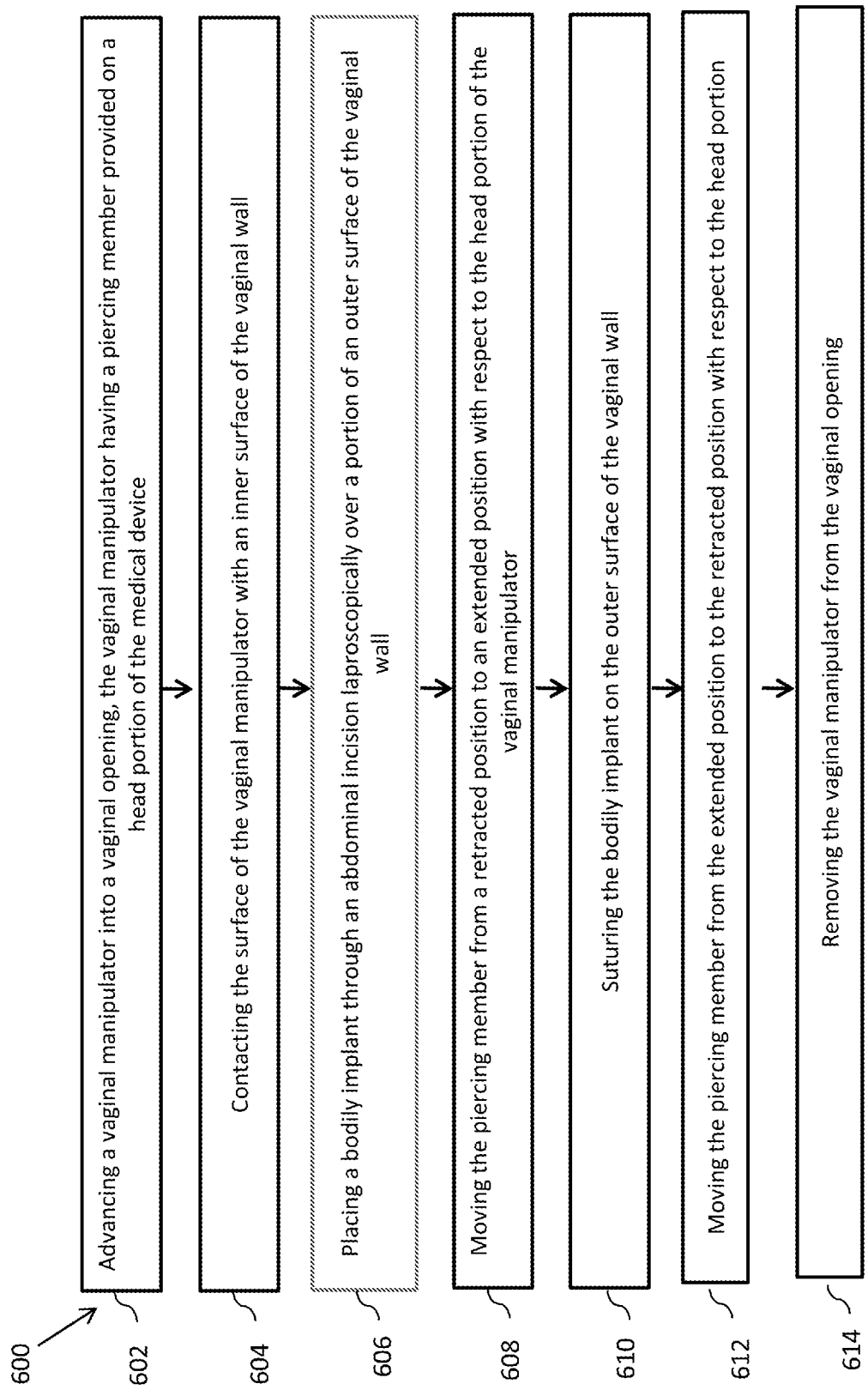
FIG. 6 illustrates a method of fixing a bodily implant to an outer surface of a vaginal wall, in accordance with an embodiment of the present invention.

FIG. 6 illustrates a method of fixing a bodily implant 228 to an outer surface of the vaginal wall 230.

Referring now to FIG. 6 in conjunction with FIGS. 5A and 5B, and FIGS. 2A-2C, a method of fixing the bodily implant 228 to the outer surface of the vaginal wall 230 using a vaginal manipulator such as the vaginal manipulator 200 is described.

The method 600 includes advancing the vaginal manipulator 200 into a body opening such as the vagina 502 of the patient at step 602. In embodiments described herein and hereafter, the vaginal manipulator 200 is used to describe the methods and procedural steps. However, the other manipulators such as 100, 300 or 400 can also be employed.

The method 600 further includes contacting the head portion 204 of the vaginal manipulator 200 to an inner surface of the vaginal wall at step 604 such that the vaginal wall 230 expands owing to a pressure exerted by the head portion 204. In some embodiments, the vaginal wall 230 may not substantially expand rather just touches to the head portion 204.

The method 600 further includes placing a bodily implant 228 through an abdominal incision laparoscopically over a portion of outer surface of the vaginal wall 230 at step 606. The bodily implant 222 can be delivered in accordance with various surgical procedures such as through abdominal, transvaginal, and the like. Further, the delivery of the bodily implant 222 can be performed through laparoscopic or laprotomic approaches. In accordance with various other embodiments, any conventional approach for delivery of the bodily implant 222 can be employed.

In some embodiments, the bodily implant 228 can be of the type of Y shaped mesh as discussed above. In accordance with some embodiments, the first arm 504 and the second arm 506 of the Y-shaped mesh are attached to the anterior and the posterior portions of the vaginal wall respectively. The third arm 508 of the Y-shaped mesh is attached to a tissue proximate the sacrum 512 of a patient and the support portion 510 of the Y-shaped mesh provide a support to the vagina 502. In accordance with other embodiments, several other types of conventionally available implants can also be used. For example, a single piece bodily implant 228 having only one elongate member can be used.

The method 600 further includes moving the piercing member 208 from the retracted position to the extended position with respect to the head portion 204 of the medical device 200 at step 608. In some embodiments, the actuating mechanism 206 can be operated from external to the body tissue for moving the piercing member 208 from the retracted position to the extended position. The piercing member 208 protrudes with respect to the head portion 204 and pierces through the vaginal wall 230, when in the extended position. In the extended position, a substantial length of the piercing member 208 comes out of the head portion 204 to a defined extent or length that depends on an amount of adjustment made by the actuating mechanism 206. In this position, the piercing member 208 pierces through the bodily implant 228 and tip portion of the piercing member 208 engages with the bodily implant 228 to help hold it temporarily till suturing process completes.

The method 600 further includes suturing the bodily implant 228 on the outer surface of the vaginal wall 230 at step 610. The method 600 can further include adjusting tensions of the first arm 504, the second arm 506 and the third arm 508. The fixation of the first arm 504, the second arm 506 and the third arm 508 provides a desired tension to the support portion 510. In some embodiments, after the first arm 504 and the second arm 506 are attached to the anterior and the posterior portions of the vaginal wall respectively, the third arm 508 is pulled toward the sacrum 512 with an appropriate tension thereby pulling the support portion 510, the first arm 504, and the second arm 506 upward. This may help in lifting disordered organs such as the anterior vaginal wall, posterior vaginal wall, cervix, and uterus. An appropriate support is thus provided to the disordered organs by the bodily implant 228.

The method 600 further includes moving the piercing member 208 from the extended position to the retracted position with respect to the head portion 204 at step 614. The piercing member 208 comes out of the vaginal wall 230 the method 600 further includes removing the vaginal manipulator 200 from the vaginal opening at step 614. The steps of this method can be altered by the medical practitioner to achieve the same result or similar results. For example, the mesh may be situated and then held by deploying needles or the like through the walls from the inside of the vagina of the patient. Any other steps, such as suturing or coupling may follow.

In some embodiments, the piercing member 408 may be coupled to the suture 436 before or after insertion and placement of the vaginal manipulator 400 into the patient's body. The piercing member 408 is configured to move the suture 436 across the vaginal wall 430 when the piercing member 408 is in its extended position. This causes suturing and affixing the bodily implant 422 on the outer surface of the vaginal wall 430.

In some embodiments, the vaginal manipulator 400 is configured to be inserted into the body (contacting the inner surface of the vaginal wall) in the retracted position. The vaginal manipulator 400 is then moved to a partially extended position where the piercing member 408 extends or protrudes out of the head portion 404 and pierces through the vaginal wall 430. The bodily implant 428 can then be placed over the piercing member 408 on the outer surface of the vaginal wall 430 in such a manner that the piercing member 408 engages with the bodily implant 428. At this state, the suture 436 is coupled to the piercing member 408. In some other embodiments, the bodily implant 428 can first be placed laparoscopically over a portion of the outer surface of the vaginal wall 430. The piercing member 408 of the vaginal manipulator 400 is then protruded out with respect to the head portion 404 to an extent that it is capable of piercing through the vaginal wall 430 over the bodily implant 428. The piercing member 408 is then brought to the retracted position such that the suture 436 traverses a path from the outer surface of the vaginal wall 430 to the inner surface of the vaginal wall. The suture 436 or suture ends can then be tied. In this embodiment, the suture 436 crosses or pierces through the vaginal wall 430 once while going from the inner surface of the vaginal wall to the outer surface of the vaginal wall 430. And, thus, a suture 436 is placed to help affix the bodily implant 428 on the outer surface. Simultaneously, the vaginal manipulator 400 also assists in holding the bodily implant 428 temporarily by providing a support through frictional resistance provided by engagement of the piercing member 408 with the mesh temporarily till the piercing member 408 places the suture 436 and secures it firmly. Subsequently, even when the temporarily force due to engagement is removed by removing the vaginal manipulator 400, the bodily implant 426 is still held at its location.

In some other embodiments, the suture 436 can be coupled to the piercing member 408 before insertion into the body. The subsequent steps are similar as above except that when the piercing member 408 is brought to the partially extended position, the piercing member 408 traverses from the inner surface of the vaginal wall to the outer surface of the vaginal wall 430 with the suture 436 piercing through the vaginal wall 430. And, when the piercing member 408 is moved to the completely extended position the piercing member 408 further extends in a manner that due to the curved nature of the piercing member 408, the tip portion of the piercing member 408 reaches proximate a proximal portion of the piercing member 408. In this manner, the suture 436 traverses a path back from the outer surface of the vaginal wall 430 to the inner surface of the vaginal wall. The traversed path is different than while moving the piercing member 408 from the inner surface to the outer surface of the vaginal 430. The suture 436 can then be tied. In this embodiment, the suture 436 traverses a cyclic path and can tie the bodily implant 428 in a better and more secured way.

In some embodiments, a vaginal manipulator is configured to be inserted through a vaginal opening. The vaginal manipulator includes an elongated portion and a head portion. The elongated portion has a proximal end portion and a distal end portion. The elongated portion has an actuating mechanism. The head portion extends from the distal end portion of the elongated portion. The head portion includes a linear piercing member. The piercing member is configured to temporarily help retain a bodily implant proximate an outer surface of a vaginal wall. The piercing member is configured to move from a refracted position to an extended position with respect to the head portion. The actuating mechanism is operatively coupled to the piercing member and is configured to move the piercing member from its retracted position to its extended position.

In some embodiments, the elongated portion is a handle of the vaginal manipulator and is configured to be held by an operator external from a body tissue. In some embodiments, the elongated portion has a first width and the head portion has a second width such that the second width is greater than the first width.

In some embodiments, the actuating mechanism includes one of a lever and a knob configured to move the piercing member from external to a body tissue and move the piercing member from the retracted position tithe extended position.

In some embodiments, the piercing member is a needle that is configured to protrude out with respect to the head portion, when in the extended position, and pierce through the vaginal wall.

In some embodiments, the bodily implant is configured to be placed laproscopically over the piercing member. When the piercing member is in the extended position, and extends through the outer surface of the vaginal wall such that the bodily implant is temporarily retained to the outer surface of the vaginal wall by the vaginal manipulator. In some embodiments, the bodily implant is made from one of a polypropylene and a biologic material.

In some embodiments, the piercing member is disposed on the head portion and the piercing member includes a first needle configured to extend from within the head portion toward first surface of the head portion.

In some embodiments, the device includes a second piercing member disposed on the head portion. The second piercing member includes a second needle configured to extend from within the head portion toward second surface of the head portion. The second surface and the first surface being substantially opposite to one another.

In some embodiments, a vaginal manipulator is configured to be inserted through a vaginal opening. The vaginal manipulator includes an elongated portion having a proximal end portion and a distal end portion, the elongated portion having an actuating mechanism; a head portion extending from the distal end portion of the elongated portion, wherein the head portion is configured to contact an inner surface of a vaginal wall, the head portion including a piercing member configured to move between a retracted position and an extended position with respect to the head portion; and a suture coupled to the piercing member such that the piercing member is configured to move the suture through the vaginal wall when the piercing member is moved from the retracted position to the extended position, thereby affixing bodily implant coupled to the suture to the outer surface of the vaginal wall.

In some embodiments, the piercing member is a curved needle configured to protrude out from the head portion in a curvilinear manner. In some embodiments, the curved needle is configured to pierce through the vaginal wall such that a tip portion of the curved needle passes through the bodily implant placed on the outer surface of the vaginal wall and affix the bodily implant.

In some embodiments, a method of fixing a bodily implant to an outer surface of a vaginal wall includes advancing a vaginal manipulator into a vaginal opening, the vaginal manipulator having a piercing member provided on the head portion of the vaginal manipulator and configured to move from within the head portion to a location external to the head portion; placing a bodily implant through an abdominal incision laproscopically over a portion of an outer surface of the vaginal wall; moving the piercing member from a retracted position to an extended position with respect to the head portion of the vaginal manipulator such that the piercing member protrudes outward with respect to the head portion and pierces through the vaginal wall when in the extended position; suturing the bodily implant on the outer surface of the vaginal wall; and moving the piercing member from the extended position to the retracted position with respect to the head portion such that the piercing member comes out of the vaginal wall.

In some embodiments, the method includes contacting the head portion to an inner surface of the vaginal wall such that the vaginal wall expands owing to a pressure exerted by the head portion.

In some embodiments, the actuating mechanism includes one of a lever or a sliding member and a knob that is configured to be operated for switching the piercing member between the retracted position and the extended position.

In some embodiments, the method includes removing the vaginal manipulator from the vaginal opening.

In some embodiments, the bodily implant is a mesh-based device. In some embodiments, the mesh-based device includes a Y-shaped mesh. The Y-shaped mesh includes a first arm, a second arm, a third arm, and a support portion, the support portion is configured to provide a support to a vagina. The first arm and the second arm are configured to be respectively attached to an anterior and a posterior portion of the vaginal wall. The third arm is configured to be attached to a sacrum of a patient.

In some embodiments, the method includes attaching the first arm to the anterior portion of the vaginal wall using a first surface of the head portion.

In some embodiments, the method includes attaching the second arm to the posterior portion of the vaginal wall using a second surface of the head portion.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A vaginal manipulator configured to be inserted through a vaginal opening, the vaginal manipulator comprising:
    an elongated portion having a proximal end portion and a distal end portion, the elongated portion having an actuating mechanism; and
    a head portion extending from the distal end portion of the elongated portion, the head portion including a piercing member having a longitudinal axis, the piercing member includes a linear piercing member, wherein when the vaginal manipulator is situated within the vagina the piercing member is configured to temporarily help retain a bodily implant proximate an outer surface of a vaginal wall, the piercing member configured to move, along a linear path, from a retracted position in which the piercing member is internal to the head portion to an extended position in which a portion of the piercing member is external to the head portion, wherein in the extended position the piercing member is configured to extend through the vaginal wall,
    wherein the actuating mechanism is operatively coupled to the piercing member and is configured to move the piercing member from its retracted position to its extended position such that the piercing member moves in a direction along the longitudinal axis of the piercing member, the longitudinal axis of the piercing member being perpendicular to a longitudinal axis of the head portion.

2. The vaginal manipulator of claim 1, wherein the elongated portion is a handle of the vaginal manipulator and is configured to be held by an operator external from a body tissue.

3. The vaginal manipulator of claim 1, wherein the elongated portion has a surface and the head portion has a surface, the surface of the head portion being wider than any portion of the surface of the elongated portion.

4. The vaginal manipulator of claim 1, wherein the actuating mechanism includes one of a lever and a knob configured to move the piercing member from the retracted position to the extended position.

5. The vaginal manipulator of claim 1, wherein the piercing member includes a needle that is configured to protrude out with respect to the head portion, when in the extended position, and pierce through the vaginal wall.

6. The vaginal manipulator of claim 1, wherein the bodily implant is configured to be placed over the piercing member, when the piercing member is in the extended position, the piercing member is configured to extend through the outer surface of the vaginal wall such that the bodily implant is temporarily retained to the outer surface of the vaginal wall by the vaginal manipulator.

7. The vaginal manipulator of claim 1, wherein the piercing member is disposed on the head portion, the piercing member including a first needle configured to extend from within the head portion toward a first surface of the head portion.

8. The vaginal manipulator of claim 7, further comprising:
    a second piercing member disposed on the head portion, the second piercing member including a second needle configured to extend from within the head portion toward second surface of the head portion, the second surface and the first surface being substantially opposite to one another.

9. The vaginal manipulator of claim 1, wherein the piercing member includes a first piercing member and a second piercing member, the head portion including a first surface defining at least one opening such that the first piercing member extends out of the at least one opening of the first surface when the first piercing member is in the extended position, the head portion including a second surface defining at least one opening such that the second piercing member extends out of the at least one opening of the second surface when the second piercing member is in the extended position.

10. The vaginal manipulator of claim 1, wherein the piercing member is entirely linear.

11. A vaginal manipulator comprising:
    a handle having a proximal end portion and a distal end portion, the handle having an actuating mechanism; and
    a head portion extending from the distal end portion of the handle, the head portion including a piercing member operatively coupled to the actuating mechanism, the piercing member being a linear piercing member, the head portion projecting laterally from the distal end portion of the handle such that the head portion has a width greater than any width of the handle,
    the piercing member being configured to move from a first position in which the piercing member is retracted within the head portion to a second position in which at least a portion of the piercing member extends out of the head portion,
    wherein the piercing member moves only in a linear path along a longitudinal axis of the piercing member from the first position to the second position and vice versa, the longitudinal axis of the piercing member being perpendicular to a longitudinal axis of the head portion.

12. The vaginal manipulator of claim 11, wherein the piercing member includes a plurality of piercing members, the head portion including a first surface and a second surface opposite to the first surface, the first surface defining first and second openings, the second surface defining third and fourth openings, wherein portions of the plurality of piercing members extend out of the first through fourth openings when the plurality of piercing members are in the second position.

13. The vaginal manipulator of claim 11, wherein the head portion includes a first flat surface and a second flat surface opposite to the first surface, the head portion having a rectangular cross-section.

14. The vaginal manipulator of claim 11, wherein the actuating mechanism is configured to move the piecing member to a plurality of fixed positions, the plurality of fixed positions including the first position, the second position, and a third position between the first position and the second position.

15. The vaginal manipulator of claim 11, wherein the actuating mechanism extends through a lumen of the handle and the head portion.

16. A vaginal manipulator comprising:
an elongated portion having a proximal end portion and a distal end portion, the elongated portion having an actuating mechanism; and
a head portion extending from the distal end portion of the elongated portion, the head portion having a first surface defining a first opening and a second opening, the head portion having a second surface defining a first opening and a second opening, the head portion including a plurality of piercing members operatively coupled to the actuating mechanism, the plurality of piercing members including a first piercing member, a second piercing member, a third piercing member, and a fourth piercing member, the first piercing member being entirely linear,
the first and second piercing members being configured to move in a first direction from a first position in which the first and second piercing members are refracted within the first surface of the head portion to a second position in which a portion of the first piercing member extends through the first opening of the first surface and a portion of the second piercing member extends through the second opening of the first surface,
the third and fourth piercing members being configured to move in a second direction from a first position in which the third and fourth piercing members are retracted within the second surface of the head portion to a second position in which a portion of the third piercing member extends through the first opening of the second surface and a portion of the fourth piercing member extends through the second opening of the second surface, the second direction being opposite to the first direction,
wherein the first direction is a direction along a longitudinal axis of the first and second piercing members, the longitudinal axis of the first and second piercing members being perpendicular to a longitudinal axis of the head portion.

17. The vaginal manipulator of claim 16, wherein the second direction is a direction along a longitudinal axis of the third and fourth piercing members, the longitudinal axis of the third and fourth piercing members being perpendicular to the longitudinal axis of the head portion.

18. The vaginal manipulator of claim 16, wherein the first through fourth piercing members are configured to move only in linear directions from the first position to the second position.

* * * * *